(12) United States Patent  (10) Patent No.: US 9,078,740 B2
Steiner et al.  (45) Date of Patent: Jul. 14, 2015

(54) INSTRUMENTATION AND METHOD FOR POSITIONING AND SECURING A GRAFT

(71) Applicant: Howmedica Osteonics Corp., Mahwah, NJ (US)

(72) Inventors: Mark Steiner, Wellesley, MA (US); Cortny Robison, Salt Lake City, UT (US); Lindsay Rudert, Denver, CO (US); Daniel Miller, Denver, CO (US)

(73) Assignee: Howmedica Osteonics Corp., Mahwah, NJ (US)

( * ) Notice: Subject to any disclaimer, the term of this patent is extended or adjusted under 35 U.S.C. 154(b) by 236 days.

(21) Appl. No.: 13/746,096

(22) Filed: Jan. 21, 2013

(65) Prior Publication Data

US 2014/0207233 A1  Jul. 24, 2014

(51) Int. Cl.
*A61F 2/08* (2006.01)
*A61B 17/88* (2006.01)
*A61B 17/02* (2006.01)
*A61B 17/86* (2006.01)
*A61B 17/00* (2006.01)

(52) U.S. Cl.
CPC ............ *A61F 2/0805* (2013.01); *A61B 17/8875* (2013.01); *A61B 17/8615* (2013.01); *A61B 17/8645* (2013.01); *A61B 17/888* (2013.01); *A61B 2017/00314* (2013.01); *A61B 2017/0268* (2013.01); *A61F 2002/0841* (2013.01); *A61F 2002/0882* (2013.01)

(58) Field of Classification Search
CPC .................................. A61F 2/08; A61F 2/0811
USPC ............................................ 623/13.11–13.19
See application file for complete search history.

(56) References Cited

U.S. PATENT DOCUMENTS

| 749,624 | A | 1/1904 | McCullough |
| 1,308,798 | A | 7/1919 | Masland |
| 1,624,530 | A | 4/1927 | Caruso |
| 2,073,903 | A | 3/1937 | O'Neil |
| 2,250,434 | A | 7/1941 | Dugaw |
| 2,461,947 | A | 2/1949 | Weber |
| 2,515,365 | A | 7/1950 | Zublin |

(Continued)

FOREIGN PATENT DOCUMENTS

| DE | 3131496 A1 | 2/1983 |
| DE | 8903079 U1 | 5/1989 |

(Continued)

OTHER PUBLICATIONS

Canadian Office Action for Application No. 2,811,838 dated May 22, 2014.

(Continued)

*Primary Examiner* — Suzette J Gherbi
(74) *Attorney, Agent, or Firm* — Lerner, David, Littenberg, Krumholz & Mentlik, LLP

(57) ABSTRACT

In one embodiment, the present invention is a method of positioning and securing a graft to bone including the steps of: positioning the graft into a bore hole in the bone; positioning a guide wire into the bore hole in the bone; positioning a slide instrument between the guide wire and the graft; positioning a driver, and an anchor secured thereto, over the guide wire; directing the anchor along the guide wire and towards and into the bore hole; and imparting a rotational force to the anchor to secure the anchor between a sidewall of the bore hole and a portion of the graft.

21 Claims, 17 Drawing Sheets

(56) References Cited

U.S. PATENT DOCUMENTS

| | | |
|---|---|---|
| 2,547,571 A | 4/1951 | Ettinger |
| 2,773,672 A | 12/1956 | Holmes et al. |
| 2,833,284 A | 5/1958 | Springer |
| 3,384,085 A | 5/1968 | Hall |
| 3,407,889 A | 10/1968 | Hjalsten et al. |
| 3,461,875 A | 8/1969 | Hall |
| 3,554,192 A | 1/1971 | Isberner |
| 3,750,671 A | 8/1973 | Hedrick |
| 3,867,932 A | 2/1975 | Huene |
| 3,892,232 A | 7/1975 | Neufeld |
| 4,212,569 A | 7/1980 | Andersson et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,541,423 A | 9/1985 | Barber |
| 4,594,033 A | 6/1986 | Peetz et al. |
| 4,605,347 A | 8/1986 | Jodock et al. |
| 4,608,972 A | 9/1986 | Small |
| 4,611,515 A | 9/1986 | Marbourg, Jr. |
| 4,635,738 A | 1/1987 | Schillinger et al. |
| 4,646,738 A | 3/1987 | Trott |
| 4,706,659 A | 11/1987 | Matthews et al. |
| 4,728,231 A | 3/1988 | Kunimori et al. |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,842,451 A | 6/1989 | Dugger |
| 4,872,451 A | 10/1989 | Moore et al. |
| 4,946,462 A | 8/1990 | Watanabe |
| 5,002,546 A | 3/1991 | Romano |
| 5,007,911 A | 4/1991 | Baker |
| 5,030,219 A | 7/1991 | Matsen, III et al. |
| 5,037,423 A | 8/1991 | Kenna |
| 5,064,431 A | 11/1991 | Gilbertson et al. |
| 5,122,134 A | 6/1992 | Borzone et al. |
| 5,133,720 A | 7/1992 | Greenberg |
| 5,139,520 A | 8/1992 | Rosenberg |
| 5,163,940 A | 11/1992 | Bourque |
| 5,165,494 A | 11/1992 | Barr |
| 5,186,268 A | 2/1993 | Clegg |
| 5,190,548 A | 3/1993 | Davis |
| 5,203,595 A | 4/1993 | Borzone et al. |
| RE34,293 E | 6/1993 | Goble et al. |
| 5,234,435 A | 8/1993 | Seagrave, Jr. |
| 5,269,785 A | 12/1993 | Bonutti |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,409,494 A | 4/1995 | Morgan |
| 5,423,824 A | 6/1995 | Akerfeldt et al. |
| 5,437,675 A | 8/1995 | Wilson |
| 5,437,677 A | 8/1995 | Shearer et al. |
| 5,441,502 A | 8/1995 | Bartlett |
| 5,458,604 A | 10/1995 | Schmieding |
| 5,464,407 A | 11/1995 | McGuire |
| 5,466,243 A | 11/1995 | Schmieding et al. |
| 5,488,761 A | 2/1996 | Leone |
| 5,520,693 A | 5/1996 | McGuire et al. |
| 5,527,316 A | 6/1996 | Stone et al. |
| 5,529,580 A | 6/1996 | Kusunoki et al. |
| 5,570,706 A | 11/1996 | Howell |
| 5,571,111 A | 11/1996 | Aboczky |
| 5,575,819 A | 11/1996 | Amis |
| 5,584,617 A | 12/1996 | Houser |
| 5,601,561 A | 2/1997 | Terry et al. |
| 5,645,545 A | 7/1997 | Bryant |
| 5,658,289 A | 8/1997 | Boucher et al. |
| 5,664,914 A | 9/1997 | Taniguchi |
| 5,667,509 A | 9/1997 | Westin |
| 5,681,315 A | 10/1997 | Szabo |
| 5,681,320 A | 10/1997 | McGuire |
| 5,683,401 A | 11/1997 | Schmieding et al. |
| 5,690,677 A | 11/1997 | Schmieding et al. |
| 5,695,513 A | 12/1997 | Johnson et al. |
| 5,707,374 A | 1/1998 | Schmidt |
| 5,713,905 A | 2/1998 | Goble et al. |
| 5,725,530 A | 3/1998 | Popken |
| 5,732,606 A | 3/1998 | Chiang |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,788,699 A | 8/1998 | Bobst et al. |
| 5,797,918 A | 8/1998 | McGuire et al. |
| 5,836,953 A | 11/1998 | Yoon |
| 5,851,208 A | 12/1998 | Trott |
| 5,888,034 A | 3/1999 | Greenberg |
| 5,895,179 A | 4/1999 | Gschwend et al. |
| 5,897,574 A | 4/1999 | Bonutti |
| 5,906,626 A | 5/1999 | Carrillo |
| 5,908,423 A | 6/1999 | Kashuba et al. |
| 5,928,244 A | 7/1999 | Tovey et al. |
| 5,941,139 A | 8/1999 | Vodehnal |
| 5,941,883 A | 8/1999 | Sklar |
| 5,947,659 A | 9/1999 | Mays |
| 5,951,559 A | 9/1999 | Burkhart |
| 5,993,451 A | 11/1999 | Burkhart |
| 6,010,515 A | 1/2000 | Swain et al. |
| 6,019,767 A | 2/2000 | Howell |
| 6,030,406 A | 2/2000 | Davis et al. |
| 6,053,922 A | 4/2000 | Krause et al. |
| 6,068,642 A | 5/2000 | Johnson et al. |
| 6,120,511 A | 9/2000 | Chan |
| 6,146,385 A | 11/2000 | Torrie et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,254,604 B1 | 7/2001 | Howell |
| 6,258,093 B1 | 7/2001 | Edwards et al. |
| 6,270,501 B1 | 8/2001 | Freiberg et al. |
| 6,306,138 B1 | 10/2001 | Clark et al. |
| 6,343,482 B1 | 2/2002 | Endo et al. |
| 6,352,538 B2 | 3/2002 | McGuire et al. |
| 6,358,253 B1 | 3/2002 | Torrie et al. |
| 6,364,886 B1 | 4/2002 | Sklar |
| 6,383,188 B2 | 5/2002 | Kuslich et al. |
| 6,416,517 B2 | 7/2002 | Harder et al. |
| 6,419,678 B1 | 7/2002 | Asfora |
| 6,419,684 B1 | 7/2002 | Heisler et al. |
| 6,431,801 B2 | 8/2002 | Vasudeva et al. |
| 6,436,100 B1 | 8/2002 | Berger |
| 6,440,138 B1 | 8/2002 | Reiley et al. |
| 6,440,141 B1 | 8/2002 | Philippon |
| 6,447,518 B1 | 9/2002 | Krause et al. |
| 6,474,425 B1 | 11/2002 | Truax et al. |
| 6,478,800 B1 | 11/2002 | Fraser et al. |
| 6,494,272 B1 | 12/2002 | Eppink et al. |
| 6,558,386 B1 | 5/2003 | Cragg |
| 6,558,390 B2 | 5/2003 | Cragg |
| 6,575,979 B1 | 6/2003 | Cragg |
| 6,610,080 B2 | 8/2003 | Morgan |
| 6,660,023 B2 | 12/2003 | McDevitt et al. |
| 6,712,822 B2 | 3/2004 | Re et al. |
| 6,740,090 B1 | 5/2004 | Cragg et al. |
| 6,746,451 B2 | 6/2004 | Middleton et al. |
| 6,780,188 B2 | 8/2004 | Clark et al. |
| 6,783,533 B2 | 8/2004 | Green et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,863,672 B2 | 3/2005 | Reiley et al. |

(56) References Cited

U.S. PATENT DOCUMENTS

| | | |
|---|---|---|
| 6,874,978 B2 | 4/2005 | Gongola |
| 6,878,150 B1 | 4/2005 | McGuire et al. |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,960,214 B2 | 11/2005 | Burkinshaw |
| 7,008,431 B2 | 3/2006 | Simonson |
| 7,018,144 B2 | 3/2006 | Sasagawa et al. |
| 7,025,770 B2 | 4/2006 | McGuire et al. |
| 7,029,479 B2 | 4/2006 | Tallarida et al. |
| 7,041,107 B2 | 5/2006 | Pohjonen et al. |
| 7,048,754 B2 | 5/2006 | Martin et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,204,839 B2 | 4/2007 | Dreyfuss et al. |
| 7,241,297 B2 | 7/2007 | Shaolian et al. |
| 7,258,692 B2 | 8/2007 | Thelen et al. |
| 7,261,016 B2 | 8/2007 | Miller |
| 7,309,338 B2 | 12/2007 | Cragg |
| 7,326,215 B2 | 2/2008 | Myers et al. |
| 7,331,263 B2 | 2/2008 | Erickson et al. |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 * | 4/2009 | Re et al. ............... 623/13.14 |
| 7,563,266 B2 | 7/2009 | Camino et al. |
| 7,585,300 B2 | 9/2009 | Cha |
| 7,604,636 B1 | 10/2009 | Walters et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,515 B2 | 1/2010 | Mack et al. |
| 7,666,189 B2 | 2/2010 | Gerber et al. |
| 7,776,049 B1 | 8/2010 | Curran et al. |
| 7,879,037 B2 | 2/2011 | Brunnett et al. |
| 7,892,235 B2 | 2/2011 | Ellis |
| 7,909,547 B2 | 3/2011 | Jordan et al. |
| 7,918,874 B2 | 4/2011 | Siegal |
| 7,963,967 B1 | 6/2011 | Woods |
| 7,981,117 B2 | 7/2011 | Newton et al. |
| 8,002,733 B2 | 8/2011 | Kraft et al. |
| 8,043,253 B2 | 10/2011 | Kraft et al. |
| 8,057,500 B2 | 11/2011 | Mitusina |
| 8,070,750 B2 | 12/2011 | Wenstrom, Jr. et al. |
| 8,109,700 B2 | 2/2012 | Jordan et al. |
| 8,114,088 B2 | 2/2012 | Miller |
| 8,123,750 B2 | 2/2012 | Norton et al. |
| 8,128,640 B2 | 3/2012 | Harris et al. |
| 8,133,231 B2 | 3/2012 | Martinek et al. |
| 8,172,846 B2 | 5/2012 | Brunnett et al. |
| 8,282,679 B2 | 10/2012 | Denison |
| 8,282,981 B2 | 10/2012 | Andreacchi |
| 8,287,840 B2 | 10/2012 | Zhang et al. |
| 8,293,226 B1 | 10/2012 | Basu et al. |
| 8,293,260 B2 | 10/2012 | Wang |
| 8,293,318 B1 | 10/2012 | Hsu et al. |
| 8,298,466 B1 | 10/2012 | Yang et al. |
| 8,298,483 B2 | 10/2012 | Freeman et al. |
| 8,298,607 B2 | 10/2012 | Kerrigan et al. |
| 8,303,296 B2 | 11/2012 | Kleiner et al. |
| 8,303,505 B2 | 11/2012 | Webler et al. |
| 8,303,509 B2 | 11/2012 | Webler et al. |
| 8,303,624 B2 | 11/2012 | Fortson |
| 8,303,644 B2 | 11/2012 | Lord et al. |
| 8,308,683 B2 | 11/2012 | Leonard et al. |
| 8,308,708 B2 | 11/2012 | Leonhardt et al. |
| 8,311,312 B1 | 11/2012 | Richardson |
| 8,312,942 B2 | 11/2012 | Ho et al. |
| 8,313,791 B2 | 11/2012 | Papp |
| 8,318,088 B2 | 11/2012 | Freeman et al. |
| 8,323,327 B2 | 12/2012 | Bei et al. |
| 8,323,330 B2 | 12/2012 | Fitzgerald et al. |
| 8,323,459 B2 | 12/2012 | Andreacchi et al. |
| 8,323,676 B2 | 12/2012 | Lim et al. |
| 8,323,678 B2 | 12/2012 | Wang et al. |
| 8,328,863 B2 | 12/2012 | Abunassar |
| 8,333,984 B2 | 12/2012 | Hossainy et al. |
| 8,337,739 B2 | 12/2012 | Wang et al. |
| 8,337,937 B2 | 12/2012 | Pacetti |
| 8,343,529 B2 | 1/2013 | Hossainy et al. |
| 8,343,530 B2 | 1/2013 | Wang et al. |
| 8,366,713 B2 | 2/2013 | Long et al. |
| 8,394,129 B2 | 3/2013 | Morgenstern Lopez et al. |
| 8,409,253 B2 | 4/2013 | Stone et al. |
| 8,512,340 B2 | 8/2013 | Easley et al. |
| 8,518,087 B2 | 8/2013 | Lopez et al. |
| 8,562,645 B2 | 10/2013 | Stone et al. |
| 8,597,333 B2 | 12/2013 | Morgenstern Lopez et al. |
| 8,801,800 B2 * | 8/2014 | Bagga et al. ............... 623/23.48 |
| 2002/0019635 A1 | 2/2002 | Wenstrom et al. |
| 2002/0183758 A1 | 12/2002 | Middleton et al. |
| 2002/0188301 A1 | 12/2002 | Dallara et al. |
| 2003/0176919 A1 | 9/2003 | Schmieding |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0149093 A1 | 8/2004 | Tang |
| 2004/0193168 A1 | 9/2004 | Long et al. |
| 2004/0193217 A1 | 9/2004 | Lubbers et al. |
| 2004/0208717 A1 | 10/2004 | Greenhalgh |
| 2004/0260300 A1 | 12/2004 | Gorensek et al. |
| 2004/0267277 A1 | 12/2004 | Zannis et al. |
| 2005/0015153 A1 | 1/2005 | Goble et al. |
| 2005/0038427 A1 | 2/2005 | Perriello et al. |
| 2005/0070906 A1 | 3/2005 | Clark et al. |
| 2005/0080400 A1 | 4/2005 | Corcoran et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2005/0261604 A1 | 11/2005 | Stephens et al. |
| 2006/0004369 A1 | 1/2006 | Patel et al. |
| 2006/0015110 A1 | 1/2006 | Pepper |
| 2006/0074434 A1 | 4/2006 | Wenstrom et al. |
| 2006/0100631 A1 | 5/2006 | Sullivan et al. |
| 2006/0178748 A1 | 8/2006 | Dinger et al. |
| 2006/0212055 A1 | 9/2006 | Karabey et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0260259 A1 | 11/2007 | Fanton et al. |
| 2007/0276392 A1 | 11/2007 | Beyar et al. |
| 2007/0288031 A1 | 12/2007 | Dreyfuss et al. |
| 2008/0027446 A1 | 1/2008 | Stone et al. |
| 2008/0027457 A1 | 1/2008 | Dienst et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0071282 A1 | 3/2008 | Assell et al. |
| 2008/0109037 A1 | 5/2008 | Steiner et al. |
| 2008/0114364 A1 | 5/2008 | Goldin et al. |

(56) References Cited

U.S. PATENT DOCUMENTS

| | | |
|---|---|---|
| 2008/0140078 A1 | 6/2008 | Nelson et al. |
| 2008/0147071 A1 | 6/2008 | Serra et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0243163 A1 | 10/2008 | Masseglia et al. |
| 2008/0249481 A1 | 10/2008 | Crainich et al. |
| 2008/0275453 A1 | 11/2008 | Lafosse et al. |
| 2008/0306483 A1 | 12/2008 | Iannarone |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0076514 A1 | 3/2009 | Haines |
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0143784 A1 | 6/2009 | Petersen et al. |
| 2009/0149858 A1 | 6/2009 | Fanelli et al. |
| 2009/0157081 A1 | 6/2009 | Homan et al. |
| 2009/0160112 A1 | 6/2009 | Ostrovsky |
| 2009/0171359 A1 | 7/2009 | Sterrett |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0222013 A1 | 9/2009 | Graf et al. |
| 2009/0234451 A1* | 9/2009 | Manderson ............... 623/13.14 |
| 2009/0248029 A1 | 10/2009 | Paulos |
| 2009/0265002 A1* | 10/2009 | Re et al. .................... 623/13.14 |
| 2009/0306671 A1 | 12/2009 | McCormack et al. |
| 2009/0312763 A1 | 12/2009 | McCormack et al. |
| 2009/0312792 A1 | 12/2009 | Fallin et al. |
| 2009/0326538 A1 | 12/2009 | Sennett et al. |
| 2010/0049196 A1 | 2/2010 | Re |
| 2010/0049203 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0121332 A1 | 5/2010 | Crainich et al. |
| 2010/0121333 A1 | 5/2010 | Crainich et al. |
| 2010/0152739 A1 | 6/2010 | Sidebotham et al. |
| 2010/0191241 A1 | 7/2010 | McCormack et al. |
| 2010/0241121 A1 | 9/2010 | Logan et al. |
| 2010/0249786 A1 | 9/2010 | Schmieding et al. |
| 2010/0262146 A1 | 10/2010 | Tulkis |
| 2010/0292731 A1 | 11/2010 | Gittings et al. |
| 2011/0015674 A1 | 1/2011 | Howard et al. |
| 2011/0015675 A1 | 1/2011 | Howard et al. |
| 2011/0087247 A1 | 4/2011 | Fung et al. |
| 2011/0106089 A1 | 5/2011 | Brunnett et al. |
| 2011/0208194 A1 | 8/2011 | Steiner et al. |
| 2011/0213416 A1 | 9/2011 | Kaiser |
| 2011/0218538 A1 | 9/2011 | Sherman et al. |
| 2011/0270293 A1 | 11/2011 | Malla et al. |
| 2011/0319896 A1 | 12/2011 | Papenfuss et al. |
| 2012/0004672 A1 | 1/2012 | Giap et al. |
| 2012/0053641 A1 | 3/2012 | Meridew |
| 2012/0071976 A1* | 3/2012 | May et al. ................. 623/13.14 |
| 2012/0095556 A1* | 4/2012 | Re et al. .................... 623/13.14 |
| 2012/0109142 A1 | 5/2012 | Dayan |
| 2012/0150301 A1 | 6/2012 | Gamache et al. |
| 2012/0179254 A1* | 7/2012 | Saliman ..................... 623/13.12 |
| 2012/0203231 A1 | 8/2012 | Long et al. |
| 2012/0203288 A1 | 8/2012 | Lange et al. |
| 2012/0253355 A1 | 10/2012 | Murray et al. |
| 2012/0261858 A1 | 10/2012 | Roberts et al. |
| 2012/0263759 A1 | 10/2012 | Hossainy et al. |
| 2012/0265205 A1 | 10/2012 | Steiner et al. |
| 2012/0265291 A1 | 10/2012 | Kramer-Brown et al. |
| 2012/0273467 A1 | 11/2012 | Baxter et al. |
| 2012/0274001 A1 | 11/2012 | Prabhu |
| 2012/0277358 A1 | 11/2012 | Wang |
| 2012/0283634 A1 | 11/2012 | Magana et al. |
| 2012/0283700 A1 | 11/2012 | Pawluk |
| 2012/0285123 A1 | 11/2012 | Wang et al. |
| 2012/0285609 A1 | 11/2012 | Wang |
| 2012/0285836 A1 | 11/2012 | von Oepen |
| 2012/0289932 A1 | 11/2012 | Claude et al. |
| 2012/0290063 A1 | 11/2012 | Wang et al. |
| 2012/0290070 A1 | 11/2012 | Wang et al. |
| 2012/0290071 A1 | 11/2012 | Wang et al. |
| 2012/0290073 A1 | 11/2012 | Wang |
| 2012/0290075 A1 | 11/2012 | Mortisen et al. |
| 2012/0294759 A1 | 11/2012 | Lam et al. |
| 2012/0296312 A1 | 11/2012 | Claude et al. |
| 2012/0296313 A1 | 11/2012 | Andreacchi et al. |
| 2012/0296347 A1 | 11/2012 | Roorda et al. |
| 2012/0296372 A1 | 11/2012 | Ziobro |
| 2012/0296373 A1 | 11/2012 | Roorda et al. |
| 2012/0296374 A1 | 11/2012 | Ziobro et al. |
| 2012/0299226 A1 | 11/2012 | Wang et al. |
| 2012/0302955 A1 | 11/2012 | Liu et al. |
| 2012/0302994 A1 | 11/2012 | Wilson et al. |
| 2012/0303054 A1 | 11/2012 | Wilson et al. |
| 2012/0303114 A1 | 11/2012 | Wang et al. |
| 2012/0310142 A1 | 12/2012 | Hossainy et al. |
| 2012/0316635 A1 | 12/2012 | Jow et al. |
| 2012/0319333 A1 | 12/2012 | Huang et al. |
| 2012/0321778 A1 | 12/2012 | Kerrigan et al. |
| 2012/0324696 A1 | 12/2012 | Liu et al. |
| 2012/0328769 A1 | 12/2012 | Kerrigan et al. |
| 2012/0328770 A1 | 12/2012 | Hsu et al. |
| 2012/0330404 A1 | 12/2012 | Wang |
| 2012/0330405 A1 | 12/2012 | Pacetti |
| 2013/0005218 A1 | 1/2013 | von Oepen et al. |
| 2013/0006149 A1 | 1/2013 | Purtzer |
| 2013/0006220 A1 | 1/2013 | Yribarren et al. |
| 2013/0008780 A1 | 1/2013 | Andreacchi et al. |
| 2013/0011467 A1 | 1/2013 | Zhang et al. |
| 2013/0011545 A1 | 1/2013 | Andreacchi |
| 2013/0013055 A1 | 1/2013 | Pacetti et al. |
| 2013/0116730 A1 | 5/2013 | Denham et al. |
| 2013/0158601 A1 | 6/2013 | Stone et al. |
| 2013/0190818 A1 | 7/2013 | Norton |
| 2014/0135835 A1 | 5/2014 | Stone et al. |
| 2014/0163679 A1* | 6/2014 | Re et al. .................... 623/13.14 |

FOREIGN PATENT DOCUMENTS

| | | |
|---|---|---|
| DE | 4231101 A1 | 3/1994 |
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 1155776 A2 | 11/2001 |
| EP | 1174584 A2 | 1/2002 |
| EP | 1369089 A2 | 12/2003 |
| EP | 1398455 A2 | 3/2004 |
| EP | 2286742 A1 | 2/2011 |
| FR | 1166884 A | 11/1958 |
| FR | 2606996 A1 | 5/1988 |
| FR | 2676638 A1 | 11/1992 |
| GB | 2093353 A | 9/1982 |
| WO | 9628100 A1 | 9/1996 |
| WO | 9704908 A1 | 2/1997 |
| WO | 0024327 A2 | 5/2000 |
| WO | 00/44291 A1 | 8/2000 |
| WO | 0128457 A1 | 4/2001 |
| WO | 0160268 A1 | 8/2001 |
| WO | 03007861 A1 | 1/2003 |
| WO | 03086221 A1 | 10/2003 |
| WO | 2007/010389 A1 | 1/2007 |
| WO | 2008128075 A1 | 10/2008 |
| WO | 2009105880 A1 | 9/2009 |

OTHER PUBLICATIONS

Partial European Search Report for Application No. EP14151822 dated May 16, 2014.
Biomet Sports Medicine: Micromax Flex Suture Anchor, (2008).

(56) References Cited

OTHER PUBLICATIONS

Burkinshaw, U.S. Appl. No. 60/418,545, filed Oct. 15, 2002.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
Cole et al., American Journal of Sports Medicine, vol. XX, No. X, 2011.
European Search Report, EP 10173568, dated Nov. 30, 2010.
Extended European Search Report for Application No. EP 12164104 dated Jul. 11, 2012.
HHS Tube, Fort Wayne Metals Research Products Corp., 2009.
International Search Report PCT/US2010/042264, dated Sep. 30, 2010.
Medtronic, The VISAO High-Speed Otologic Drill Catalog, 2007.
U.S. Appl. No. 13/085,882, filed Apr. 13, 2011.
U.S. Appl. No. 13/368,730, filed Feb. 8, 2012.

\* cited by examiner

INSTRUMENTATION AND METHOD FOR POSITIONING AND SECURING A GRAFT

BACKGROUND OF THE INVENTION

The present invention relates generally to orthopedic instrumentation, systems, kits and methods for repairing soft tissue injuries including positioning and securing a graft, such as for use in reconstructing soft tissue in a joint between bones of a patient. More specifically, the present invention relates to the positioning and securing of tendon and/or ligament grafts, and more particularly, for example, the positioning and securing of an anterior cruciate ligament (ACL) graft in the knee joint of a patient.

ACL injuries are often caused by a sudden force applied to the knee, and are a common form of injury suffered during athletic activities. The injury occurs typically when the knee is bent or twisted in an awkward direction.

Current surgical reconstruction of ACL injuries may be arthroscopic or open and commonly include the formation of two bone tunnels, one in the tibia and one in the femur, which serve as attachment points for a graft. A replacement graft, either of natural tissue or artificial materials, is typically used to replace the damaged, native soft tissue as such replacement typically has better results than attempting to repair and reuse the native tissue. In any event, commonly, the native soft tissue has extensive damage, thus limiting its usefulness, and thus is likely to be removed and replaced by a graft.

Positioning and securing a graft in a prepared bone bore hole is a typical method of performing a soft tissue repair. In a specific soft tissue repair, such as in ACL repair, it is common to use a suture to pull the graft into the bone tunnel, and the graft is then secured within the bone tunnel using a suture button and/or an interference screw. A similar method and instrumentation is employed to secure the graft in the tibial bone tunnel.

However, such methods of securing the graft have various drawbacks. For example, positioning the interference screw into the bone tunnel, and adjacent the graft, could result in damage to the graft through contact with the interference screw along a portion of the graft other than the area where the interference screw is intended to create the fixation.

Further, traditional instrumentation, such as rigid and linear instrumentation, can result in limited access to the native insertion site of the ACL, thus requiring that the knee undergo hyperflexion in order for such instrumentation to access the native site. Accessing the native site can be important to the success of the repair. Recently, instrumentation capable of flexing and navigating curved access pathways has been introduced for the repair of damaged tissue such as the ACL, labrum, or the like, including commercial products such as the VersiTomic™ Flexible Reaming System and the Twin-Loop FLEX™ Instrumentation System (both manufactured by Howmedica Osteonics Corp., Mahwah, N.J.). Such systems utilize instruments having shafts that include a flexible portion, such as on a drill shaft or the like, to achieve better access to preferred positions for the placement of bone holes and bone tunnels, soft tissue connection sites, and the like. For example, such flexible instrumentation can place a bone tunnel at the native insertion site of the ACL on the femur while allowing the knee joint to remain at a normal angle rather than in hyperflexion.

There is an increased need for further instrumentation that can achieve increased success in soft tissue repair, and particularly in ACL repair.

BRIEF SUMMARY OF THE INVENTION

Generally, the present invention includes various embodiments of instrumentation, systems, kits and methods for use in positioning and securing soft tissue relative to bone, and specifically the positioning and securing of grafts in a bore hole in bone, such as a bone tunnel through a bone. Specifically, one particular use of the various embodiments disclosed herein is for the positioning and securing of a graft, such as a replacement ACL, in a bone tunnel in the femur.

In one embodiment, the present invention includes a driver for use in a surgical procedure, the driver including a shaft having a distal portion and a proximal portion and a length extending therebetween, the shaft including a flexible portion along at least part of the length, the flexible portion including a plurality of interlocking segments; a handle connected to the proximal portion of the shaft; and a distal tip portion positioned at the distal portion of the shaft. The driver may be cannulated along at least a portion of the length, and further may extend from a proximal-most end of the shaft to a distal-most end of the distal tip, wherein the cannulation is adapted to receive a flexible guide wire therethrough. Further, the guide wire, as it is flexible, may have at least one curve along its length, wherein the drive tip and the flexible portion of the shaft are adapted to pass over the at least one curve of the guide wire. Additionally, the distal tip, or drive tip, is adapted to engage an anchor thereon, the anchor having a cannulation along its length, the cannulation of the anchor and the cannulation of the driver being substantially co-axial with one another when the anchor is engaged with the drive tip.

In a further embodiment, the present invention include an instrument for use in positioning and securing a graft, the instrument comprising a handle, a shaft extending in a distal direction from the handle, and a slide at a distal end of the shaft, the slide including a first channel sized to position at least a portion of an anchor therein and a second channel sized to position at least a portion of the graft therein, such that when the anchor is positioned within the first channel and the graft is positioned within the second channel, the anchor and graft cannot contact one another. Moreover, the first channel may include a concave surface and the second channel may include a concave surface positioned in a direction opposite the first channel. Alternatively, the first channel may include a concave surface and the second channel may include a convex surface.

Further, the first channel may be defined between a first edge and a second edge and the second channel may be defined between a third edge and a fourth edge. The first edge and second edge may have the same shape as one another. Alternatively, the first edge and second edge may have differing shapes from one another. Further, one of the first or second edges may be larger than the other of the first or second edges. In the alternative where the second channel includes a convex surface, the third and fourth edges may be shaped to give the second channel an overall generally concave shape.

Additionally, the third edge and fourth edge may have the same shape as one another. Alternatively, the third edge and fourth edge may have differing shapes from one another. The fourth edge may be larger than the third edge. Further, the first edge and third edge may have generally the same shape as one another. Also, the second edge and fourth edge may have generally the same shape as one another.

In yet a further embodiment, the present invention includes a device for use in positioning and securing a graft, the device comprising a handle at a proximal end and a slide at a distal end, the slide including a first channel having a length and a width, the width defined between a first edge and a second edge, a second channel having a length substantially equal to the length of the first channel and a width, the width defined between a third edge and a fourth edge, the first channel and second channel open to generally opposite directions of one another and offset in a lateral direction to one another.

Additionally, the second edge of the first channel may extend laterally further than the third edge of the second channel, and the fourth edge of the second channel may extend laterally, opposite the second and third edges, further than the first edge of the first channel. The lateral offset of the first and second channels may provide the slide with a low profile shape. Further, the first channel and second channel may be substantially parallel to one another. Moreover, the first channel and second channel may have open ends along the direction of their respective lengths, and the first channel and second channel may each have a substantially concave shape extending from the first edge to the second edge, and from the third edge to the fourth edge, respectively.

Continuing with this embodiment, the handle may be secured to the slide through a shaft extending between the handle and slide. When in use, the first channel may be adapted to position at least a portion of an anchor therein, and the second channel may be adapted to position at least a portion of the graft therein. Further, when the anchor and graft are positioned in the first channel and second channel, respectively, the anchor may not contact the graft. Also, the first and second channels both may have a smooth surface adapted to allow the anchor and graft, respectively, to slide therein.

In still a further embodiment, the present invention includes a device for use in positioning and securing a graft, the device comprising a handle at a proximal end and a slide at a distal end, the slide including a first channel having a length and a width, the width defined between a first edge and a second edge, a second channel having a length substantially equal to the length of the first channel and a width, the width defined between a third edge and a fourth edge, the first channel and second channel open to generally opposite directions of one another. Further, the first channel may have a concave surface and the second channel may have a convex surface. The third and fourth edges of the second channel may be shaped such that the second channel has an overall generally concave shape adapted to position the graft therein. The first channel also includes a defined first edge but a generally undefined second edge, such that the first edge forms a portion of the concave shape of the first channel but the second edge generally does not form a portion of the concave shape, but rather extends laterally and away from the first channel.

In another embodiment, the present invention includes an instrumentation system for securing a graft in a prepared bone hole, the system including a cannulated anchor capable of securing a graft in the prepared bone hole; a cannulated driver having a shaft having a length and a flexible portion positioned along its length, and a distal end capable of engaging and applying torque to the cannulated anchor; and a slide instrument having a first channel and a second channel and adapted to be positioned between the graft and the cannulated anchor such that the graft is positioned towards a side of the bone hole and the cannulated anchor is positioned towards an opposite side of the bone hole.

In a further embodiment, the present invention includes a method for positioning and securing a graft in a prepared bone hole, the method including the steps of advancing at least a first portion of the graft into the bone hole; passing a flexible guide wire into the bone hole; positioning a slide instrument between the graft and flexible guide wire such that the slide instrument separates the bone hole into a first side and a second side, such that the graft is positioned within the first side of the bone hole and the flexible guide wire is positioned within the second side of the bone hole; positioning a cannulated driver, having a flexible portion, and a cannulated anchor, engaged with a distal end of the cannulated driver, over the guide wire such that the guide wire is positioned within the cannulated anchor and at least a portion of the cannulated driver; directing the cannulated anchor along the guide wire and into the second side of the bone hole; and fixedly securing the graft in the bone hole by positioning the anchor between a portion of a bone wall of the bone hole and at least part of the first portion of the graft, wherein the part of the first portion of the graft is compressed between another portion of the bone wall of the bone hole and the anchor.

Continuing with this embodiment, the slide may minimize contact between the anchor and an at least second portion of the graft. In one example, the bone hole may be a bone tunnel formed in a distal portion of a femur and the graft may be a replacement ACL graft. Further, the anchor may be a threaded interference screw, wherein the directing and fixedly securing steps may include rotating the threaded interference screw such that the threads of the threaded interference screw engage both the part of the first portion of the graft and the portion of the bone wall of the bone hole. In one alternative, a notch may be formed along at least part of the portion of the bone wall of the bone hole either prior to the step of advancing the graft or after the step of positioning the slide, wherein the notch can maintain the position of the anchor against the portion of the bone wall of the bone hole.

In yet another embodiment, the present invention includes a method of positioning and securing a graft to bone including positioning the graft into a bore hole in the bone; positioning a guide wire into the bore hole in the bone; positioning a slide instrument between the guide wire and the graft; positioning a driver, and an anchor secured thereto, over the guide wire; directing the anchor along the guide wire and towards and into the bore hole; and imparting a rotational force to the anchor to secure the anchor between a sidewall of the bore hole and a portion of the graft.

Further to this embodiment, the slide may include a first channel and a second channel, wherein the guide wire is positioned within the first channel and the graft is positioned within the second channel such that the guide wire and graft remain separated from one another. Also, as the anchor is directed towards and into the bore hole, the anchor and graft may remain separated from one another. As the anchor is directed further into the bore hole, the anchor may be directed past the slide to contact the portion of the graft. As to the slide, the first channel may include a concave surface and the second channel may include a concave surface positioned in a direction opposite the first channel. The first channel may include a concave surface and the second channel may include a convex surface, wherein the convex surface is bounded between first and second channel edges.

Continuing with this embodiment, prior to directing the anchor towards and into the bore hole, a notch may be formed along at least a portion of the length of the bore hole, such that the anchor is directed along the notch within the bore hole. Also, the guide wire may include a curve along at least a portion of its length between a point where the guide wire enters the bore hole and an end of the guide wire, positioned outside the bone, wherein the driver can include a portion of a shaft that is flexible such that the driver can be directed over the curve in the guide wire. In one example, the anchor may be an interference screw including a threading along at least a portion of its outer surface, wherein upon imparting the rotational force, the threading engages the sidewall of the bore hole and the portion of the graft, wherein the graft comprises a bone-tendon-bone graft, and the portion of the graft engaged by the threading of the interference screw is bone. Further to this example, the bore hole may be a bone tunnel and the bone may be a femur, wherein the graft may be a replacement anterior cruciate ligament graft.

In another embodiment, the present invention includes a method of positioning and securing a graft to bone including the steps of positioning a guide wire into a bone tunnel in the bone such that a first end of the guide wire is positioned within the bone tunnel and a second end of the guide wire is positioned outside the bone tunnel; positioning at least a portion of a graft into at least a portion of the bone tunnel; positioning a slide including a first channel and a second channel between the guide wire and the graft such that the guide wire is positioned within or adjacent to the first channel and the graft is positioned within or adjacent to the second channel; directing a cannulated anchor along the guide wire towards and into the bone tunnel; and securing the anchor between a sidewall of the bone tunnel and a portion of the graft. Further, the cannulated anchor may be directed towards and into the bone tunnel using a cannulated driver, such that the guide wire passes through the cannulation of both the driver and anchor, and the guide wire may include a curve along its length, wherein the driver includes a shaft having a flexible portion such that the flexible portion may pass over the curve of the guide wire. Also, as the anchor is directed into the bone tunnel, the anchor may be positioned within the first channel of the slide such that the anchor and graft are separated from one another, and as the anchor is directed adjacent to the portion of the graft to which it is secured, the anchor may be directed past an end of the slide such that the portion of the graft and the anchor may contact one another. As to the slide, the first channel may include a concave surface and the second channel may include a concave surface positioned in a direction opposite the first channel. Alternatively, as to the slide, the first channel may include a concave surface and the second channel may include a convex surface, wherein the convex surface may be bounded between first and second channel edges.

In yet a further embodiment, the present invention includes a method of positioning and securing a graft to bone including the steps of positioning a flexible guide wire into a bore hole in the bone, the flexible guide wire having a length; positioning the graft into the bore hole in the bone; positioning a driver, and an anchor secured thereto, over the flexible guide wire, the driver including a shaft, at least a portion of which is flexible; directing the anchor along the flexible guide wire and into the bore hole; and imparting a rotational force to the anchor to secure the anchor between a sidewall of the bore hole and a portion of the graft. This method may further include the step of positioning a slide between the flexible guide wire and the graft prior to the step of positioning the driver and anchor over the guide wire. The slide may include a first channel and a second channel, wherein the guide wire is positioned within the first channel and the graft is positioned within the second channel such that the guide wire and graft remain separated from one another.

DETAILED DESCRIPTION

Figure 1:
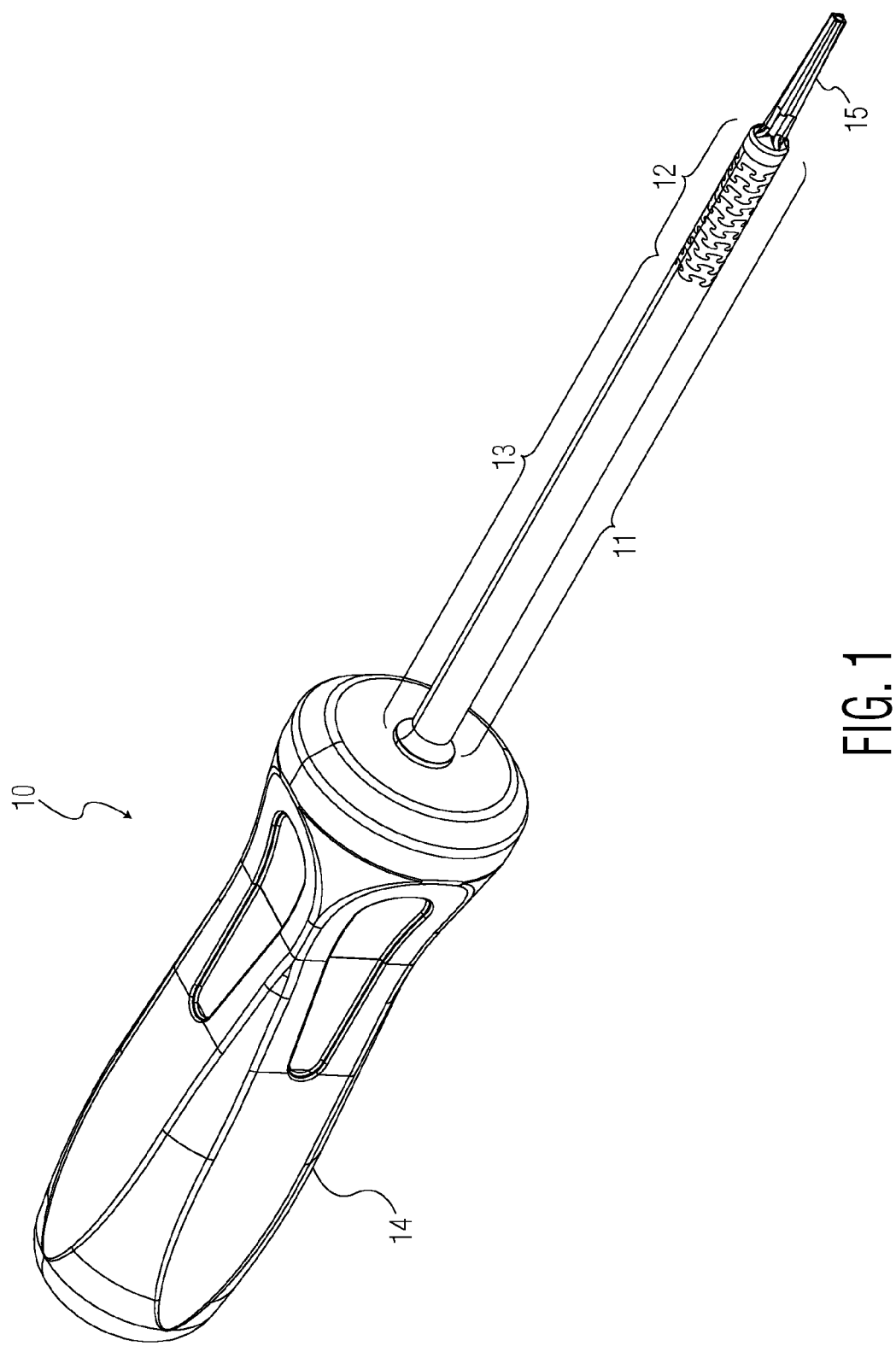
FIG. 1 illustrates one embodiment of an instrument of the present invention.

While the following exemplary embodiments of instruments, systems, kits and surgical methods may be used to repair or reconstruct any suitable type of soft tissue—such as ligaments and tendons in a knee, hip, ankle, foot, shoulder, elbow, wrist, hand, spine, or any other area of anatomy—exemplary embodiments of arthroscopic repairs or reconstructions of an ACL in a knee joint of a human patient will be used in describing the various exemplary embodiments of the disclosure below.

In most of the below embodiments, the present invention allows a surgeon to position a graft and install an anchor to secure the graft, such as an ACL replacement graft, in a previously formed tibial bone tunnel or femoral bone tunnel. The flexibility of the instrumentation allows the graft to be positioned and secured at a location near the native ACL connection sites on the femur and tibia, though other locations may be used as desired or required based on the specific circumstances of a particular patient.

While the existing soft tissue, such as the native ACL, may be repaired and remain in use within the knee joint, commonly the existing soft tissue is removed and a graft is implanted to replace the existing soft tissue. The graft may be natural soft tissue, such as autologous tissues from a portion of the patellar tendon or one of the hamstring tendons of the patient. Alternatively, allograft tissue may be obtained from a donor, or xenograft tissue may be obtained from another animal, such as a pig. Still another option for a graft could be artificial materials as are known in the art. Furthermore, the graft could include various forms, such as for example a graft made of all soft tissue, for example, a length of soft tissue which is typically folded onto itself, or a bone-tendon-bone implant which is a graft including a length of soft tissue with each end having a piece of bone attached thereto. When used herein, "graft" may be any of these types of grafts, or other suitable materials and/or structures, which are commonly used for ACL or other soft tissue replacement.

Other methods and instrumentation for soft tissue, particularly ACL, repair or reconstruction are disclosed in U.S. patent application Ser. No. 12/859,580 filed Aug. 19, 2010, U.S. patent application Ser. No. 13/085,882 filed Apr. 13 2011, U.S. patent application Ser. No. 12/821,504 filed Jun. 23, 2010, and U.S. patent application Ser. No. 12/460,310 filed Jul. 16, 2009 all owned by the same entity as this application, the disclosures of which are hereby incorporated herein by reference as if fully set forth herein. These various applications disclose various methods of, for example, creating bone bore holes such as bone tunnels for ACL surgery, positioning and securing soft tissue to bone, implanting anchors, and the like. It is envisioned that the various instrumentation and methods disclosed herein may be used in conjunction with, or as an alternative to, any of the methods and instrumentation disclosed in these pending applications incorporated by reference herein.

Referring to FIG. 1 there is shown one embodiment of an anchor inserter instrument 10, specifically a flexible driver 10, of the present invention. The driver 10 includes a distal tip portion 15, a shaft 11 and a proximal handle 14. The distal tip portion 15 includes a distal anchor interface 15 that is configured to interlock with an anchor 90 (see, for example, FIG. 4). The shaft 11 has a flexible portion 12 and a rigid portion 13. The distal tip portion 15 is fixedly secured to the flexible portion 12 through a laser weld or the like. Alternatively, the entirety of the distal portion 15 and shaft 11 may be constructed from a unitary piece, such as a monolithic length of metal tubing which is laser-cut and/or shaped to form the shaft and distal tip portion. The rigid portion 13 may be proximal to the flexible portion 12, as illustrated, and may connect to the handle 14. The handle 14 is configured in such a way that it can be gripped by an operator and used to transfer rotational force through the handle, shaft and distal tip portion and to the anchor 90 positioned on the distal portion 15 as in FIG. 5.

Figure 2:
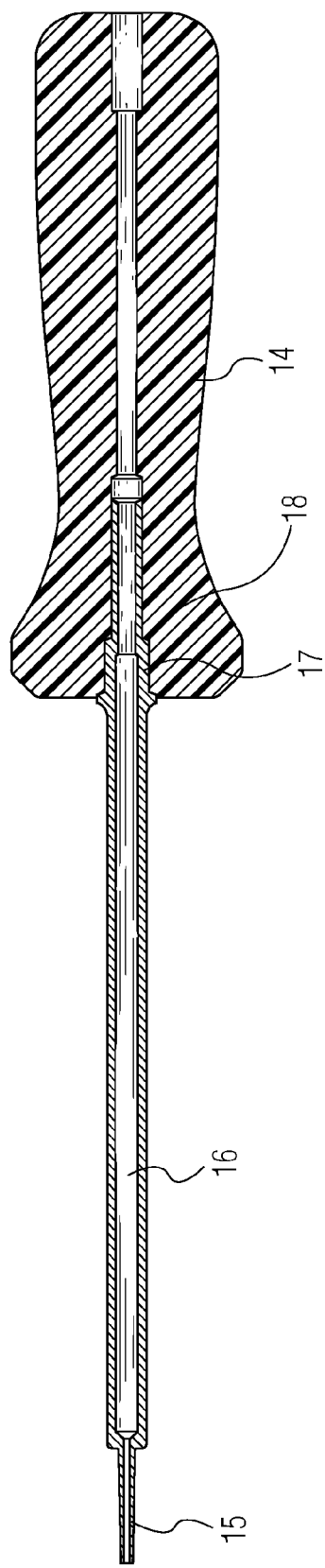
FIG. 2 illustrates a cross-sectional view of the instrument of FIG. 1.

Continuing with this embodiment, referring to FIG. 2, the flexible driver 10 may include a cannulation 16 along at least a portion of its length, though, as illustrated, it is preferred that cannulation 16 extend from the distal-most end of distal tip portion 15 through the entire length of the shaft 11 to the proximal-most end of handle 14 such that cannulation 16 may extend the entire length of the driver 10. The cannulation 16 may have a generally circular cross section and may have a generally consistent diameter along its length. However, cannulation 16 may have a differently shaped cross-section and/or a varying diameter along its length. This cannulation allows an operator to, for example, pass a guide wire 70 through the flexible driver 10, as in FIG. 25, for example. As discussed in depth below, this configuration may, for example, assist the operator to direct the anchor 90 and the flexible driver 10 into a joint and into a bore hole, such as bone tunnel 61 (see FIG. 25).

Figure 3A:
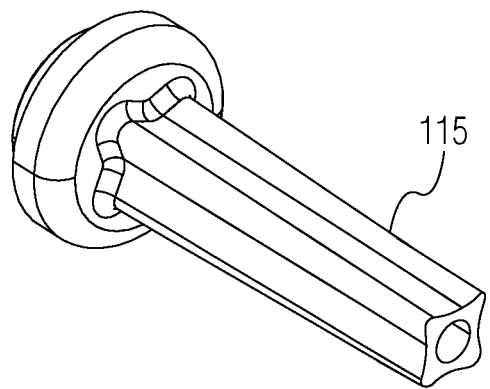
FIGS. 3A-3C illustrate various alternative embodiments of a distal tip portion of an instrument of the present invention.
Figure 3B:
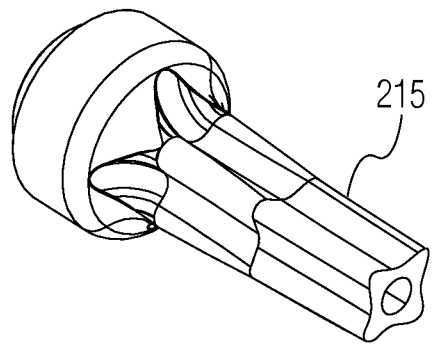
Figure 3C:
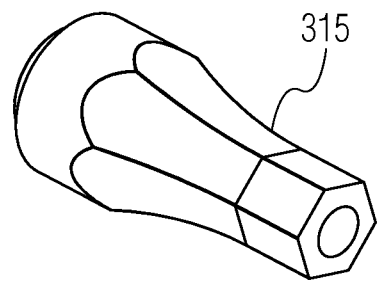

Referring to FIGS. 3A-C, there are shown various embodiments for the distal tip portion 15 of the flexible driver 10. As seen in FIG. 3A-C the distal tip portion 15 has a distal anchor interface 115, 215, 315. The distal anchor interface 115, 215, 315 is configured to interlock with an anchor 90 (see FIG. 4), which may have a matching female structure, or other suitable engaging structure, therein. The cross section of the anchor interface can have a variety of cross sectional shapes. For example, as seen in FIG. 1, the distal anchor interface 15 may be a generally square-shaped structure, whereas in FIG. 3A-B the anchor interface 115, 215 may have a generally star-shaped cross section. Alternatively, the anchor interface 315 may have a hexagonal shaped cross section as seen in FIG. 3C. In another alternative, this interlocking structure could comprise, for example, grooves running lengthwise along the distal portion of the tip or any other suitable structure capable of transferring both axial and rotational forces from the instrument 10 to the anchor 90.

Figure 4:
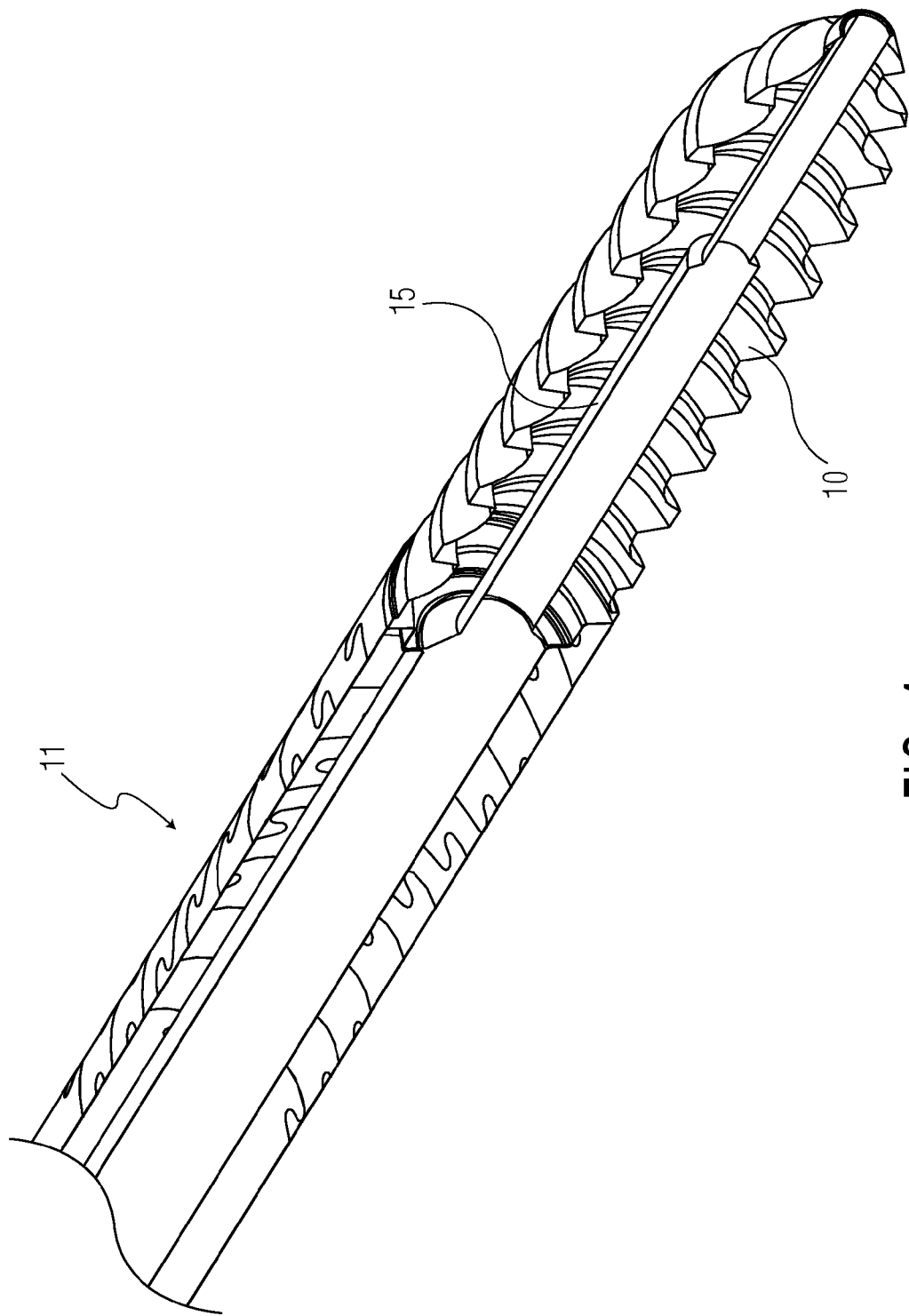
FIG. 4 illustrates a cross-sectional view of the instrument of FIG. 1 having an anchor positioned on a distal tip portion of the instrument.
Figure 5:
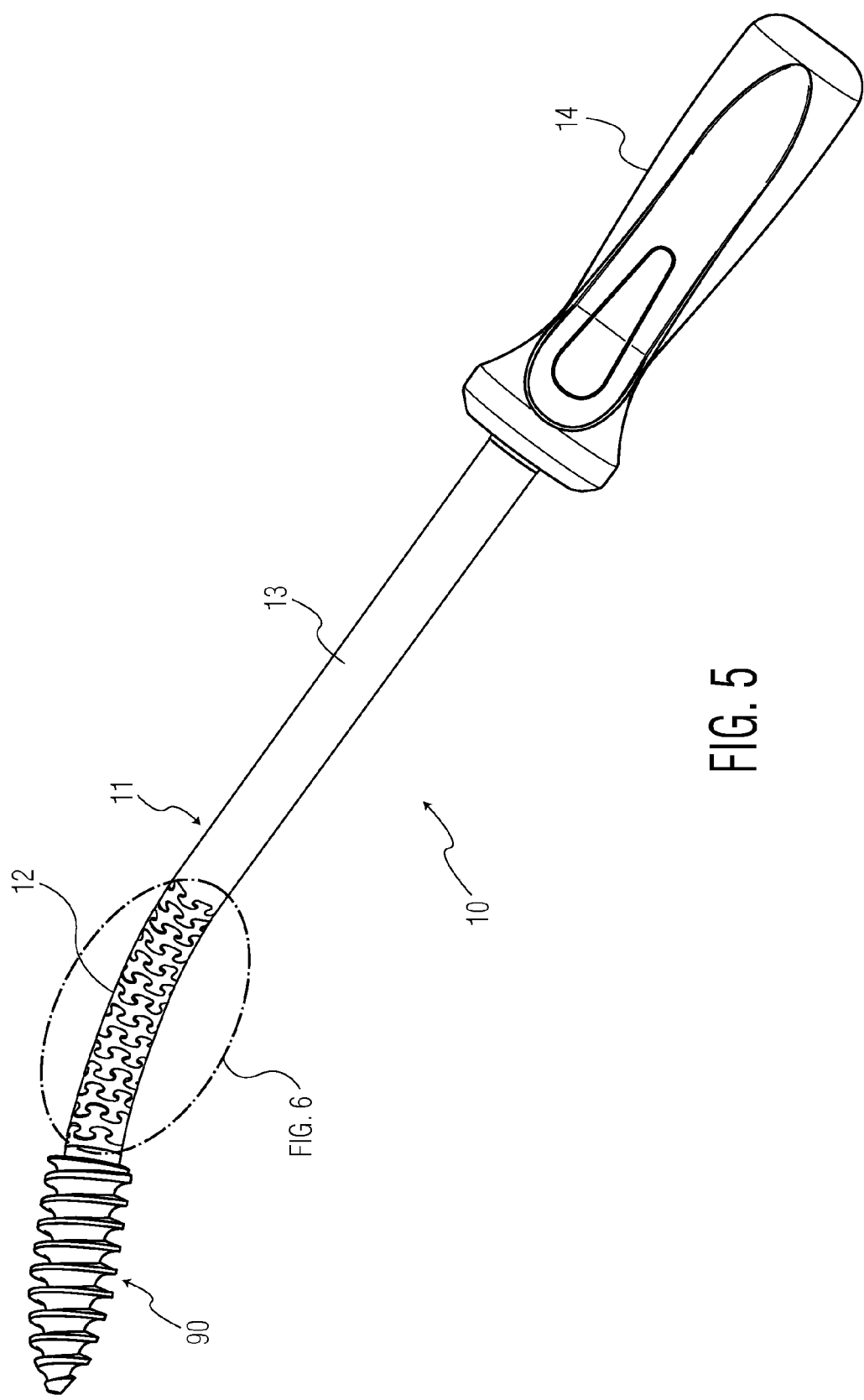
FIG. 5 illustrates an elevation view of the instrument and anchor of FIG. 4.

FIGS. 4 and 5 illustrate the distal tip portion 15 with an anchor 90 positioned thereon and overlying the anchor interface 15. The anchor 90 may have a variety of forms and sizes. For example, as illustrated, the anchor 90 is an interference screw, as in known in the art. For example, the interference screw could be a Biosteon® Interference Screw (Howmedica Osteonics Corp., Mahway, N.J.) or other such anchors. Biosteon® screws are commonly constructed of polymer, including hydroxyapatite and/or PLLA, titanium, or other such materials. The anchor could be any size suitable for a particular anatomy. For example, in ACL applications, the anchor may have a major diameter of about 6 mm, 7 mm, 8 mm, 9 mm or 10 mm, or the like. Continuing this example, the length of such an anchor may typically be between and including about 20 mm and about 30 mm, while a preferred length is between and including about 23 mm and about 28 mm. Though interference screws are preferred, other suitable anchors may also be used in place of interference screws which are suitable to implantation using a driver.

Continuing with the embodiment of FIG. 1, FIGS. 5-7 illustrate the flexible portion 12 of shaft 11 of driver 10, where the flexible portion is positioned towards the distal end of the shaft, and distal to the rigid portion 13. FIG. 5 illustrates the flexible portion positioned in a curve. The flexible portion 12 is generally formed of a series of discrete interlocking portions 20 as shown in FIGS. 7A-7B. These discrete interlocking portions may be similar to those found in the instruments of the various pending U.S. patent applications incorporated by reference herein. As such, the discrete interlocking portions are formed by laser-cutting a solid, continuous length of tube. The actual laser-cut may follow a pattern such that each portion 20 interdigitates or interlocks with each adjacent portion 20. The tubing may be hypodermic metal tubing such as copper, titanium or stainless steel, or it may be formed of a polymer or other suitable material.

Figure 6:
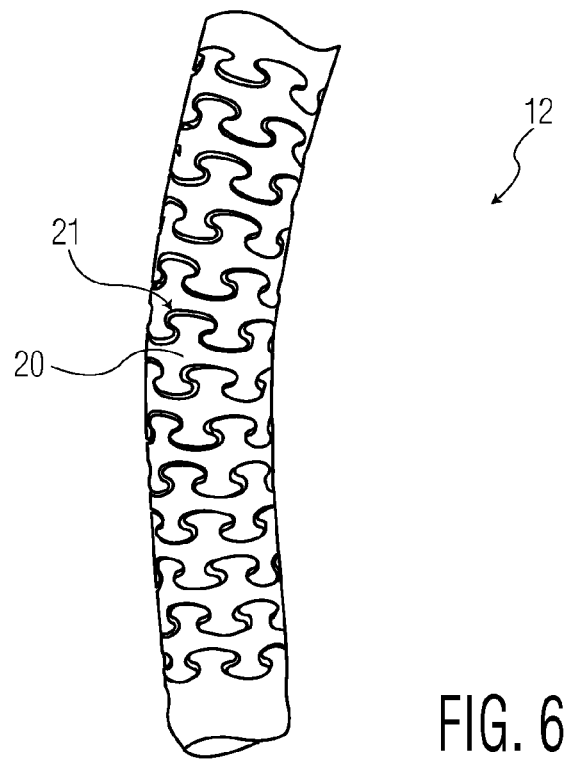
FIG. 6 illustrates a flexible portion of a shaft of the instrument of FIG. 5.
Figure 7A:
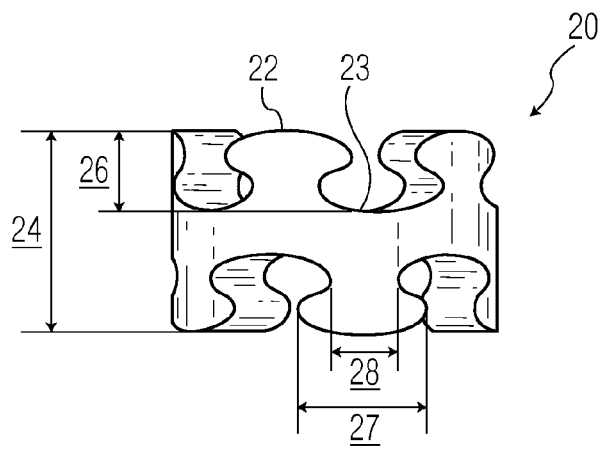
FIGS. 7A and 7B illustrate multiple views of a discrete interlocking segment of the flexible portion of FIG. 6.
Figure 7B:
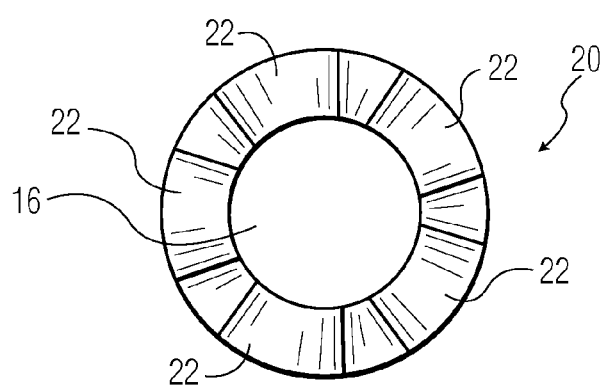

Each laser-cut may extend circumferentially around the outer surface of the tubing, and along a circuitous path, so that each cut intersects itself to form the discrete interlocking segments, as in FIGS. 6, 7A and 7B. While the cut, as illustrated, has a jig-saw-piece pattern, the cut may have at least a portion that is a wave, sinusoidal, or other shape to enhance flexibility though which may not be interlocking along that portion of the cut. In an alternate embodiment, the laser-cut could continuously spiral along the shaft and not intersect an earlier portion of the cut, though such a pattern would result in a spiral cut such that the tube remains as a continuous portion of material rather than discrete portions as is preferred. Similarly, the laser-cuts may not pass completely through the material and instead make a partial-thickness cut, though again, such a cut would not create discrete portions, but instead maintain the tubing as a continuous length of material.

Between each discrete interlocking segment 20 lies a segment gap 21. The width of the segment gap 21 may affect the maximum bend angle of the shaft such that the wider the gap, the more movement allowed between adjacent discrete segments and thus, the deeper the bend of the flexible portion. For example, when a lateral force is applied to the shaft, resulting in a curve as in FIG. 5, the force may cause the segment gap to "bottom out" along the side of the shaft forming the inner curve, while the segment gap along the side of the shaft forming the outer curve may expand to a point where the interlocking structures prevent further widening of the gap. If the segment gap is relatively large, then this curve would be more pronounced than if the segment gap is relatively small.

The segment gap 21 may be equal to the kerf created by a cutting device. A "kerf" is defined as the width of a groove made while cutting. For example, if the flexible shaft were constructed from a solid section of metal tubing, the kerf is created by the process of cutting to form the discrete interlocking segments. In one embodiment, for example, the segment gap 21 may be 0.26 mm-0.30 mm and may be equal to the kerf of a cut. In an alternate embodiment the segment gap 21 may be created by multiple passes of a cutting device, so that its width is larger than the kerf of a single cut. The cutting device, for example, may use a laser, a mechanical blade or wire or other similar device. While the above dimensions of the segment gap are preferred, the segment gap, and thus the kerf, are largely dependent on the size of the shaft and the shape of the cut. Thus, depending on these dimensions, the kerf may be from less than about 0.10 mm to about 5 mm, though other dimensions may be necessary if a particularly complex cut, and/or a large shaft, are used.

The quantity of cuts or alternatively the number of interlocking segments may also affect the maximum bend angle. As seen in FIG. 6, for example, the flexible portion 13 has 13 cuts creating 12 discrete interlocking segments. The quantity of cuts and the kerf of each cut may provide the necessary flexibility while maintaining the overall rigidity of the shaft such that it may transmit a force from the handle 14, though the shaft, and to the anchor 90. Such a combination of flexibility and rigidity may be important to ensure proper operation of the driver 10 such that axial and rotational forces may be efficiently transmitted to the anchor, and further that such forces may be transmitted when the flexible portion 12 of the shaft 11 is curved along at least a portion of its length.

Therefore, to provide one example of this combination, in creating a flexible portion 12 for use in positioning and securing an anchor in a bone tunnel in a femur, the tube may have 10 laser-cuts forming 9 discrete interlocking segments along the length of the flexible portion of the shaft, where each cut has a segment gap of 0.26 mm-0.30 mm, which allows the flexible portion of the shaft to have a maximum bend angle of 47°. Even at this bend angle, an anchor 90 engaged at the distal end may be threaded into a bore hole in a bone. The flexible portion of the shaft may be designed to have a bend angle other than 47°, though it is preferred that the bend angle be at least 25°. Put another way, the bend of the flexible portion may have a bend radius of about 47 mm, though again, this bend radius may be adjusted as necessary for particular purposes, surgical procedures, anatomy, or the like.

As discussed above, and illustrated in FIGS. 7A-7B, each discrete interlocking segment 20 of this embodiment is formed by two circuitous laser cuts forming jig-saw shaped ends. The maximum distance between these cuts yields the height 24 of the discrete interlocking segment 20. In one embodiment, for example the height 24 of the discrete interlocking segment 20 is about 7 mm, though this height may vary depending on the amount of flexibility desired, width of the shaft, and the like.

As illustrated in FIG. 7A a discrete interlocking segment 20 may include male portions 22 and female portions 23. The male portions 22 slot into the female portions of an adjacent discrete interlocking segment. Likewise, the female portions 23 receive the male portions of the adjacent segment. Each male portion 22 has a height 26, a maximum width 27 and a minimum width 28, and each of these dimensions are dependent on the size of the shaft, shape of the cut, number of male/female portions included on the circumference of the discrete interlocking segment, and other such variable. In one embodiment, for example, as to a shaft having a 6 mm width, the height 26 may preferably be about 3 mm, the maximum width 27 may preferably be about 2 mm and the minimum width 28 may be 1.33 mm. Again, these dimensions may vary based on a number of factors such that, for example, the height 26 may be between about 0.3 mm and about 30 mm, the maximum width 27 may be between about 0.2 mm and about 20 mm, and the minimum width 28 may be between about 0.1 mm and 11 mm.

As illustrated, the male portions 22 that exist on one side may be laterally offset from the female portions 23 of the opposing side of the same discrete interlocking segment 20. For example, this offset may be about 5°-8° in a clockwise direction. In an alternate embodiment the offset could be larger to create a tighter spiral appearance or smaller to create a more gradual spiral appearance. This allows a discrete interlocking segment to be rotationally offset from the discrete segments above and/or below it. In addition, each subsequent segment may be rotationally offset in the same direction from the segment above it. This offset effectively creates a "spiral" appearance along the length of the flexible shaft 11. These offsets may improve stability and may provide a smoother flexing along the length of the shaft. Further, the offset may allow for increased flexibility of the shaft by spreading the forces along the shaft more evenly over the shapes of the segments.

Alternative configurations of male and female portions are also envisioned. For example, each discrete segment may include fewer or more male and female portions (dependent on the diameter of the tubing and the size of the male and female portions created). Additionally, each of the top and bottom edges may include flat or sinusoidal portions which do not include male or female portions along at least a portion.

In addition, the quantity of male portions on one side of a discrete interlocking segment need not match the number of male portions on the opposite side of the same segment. This would occur, for example, if each subsequent cut, and thus each subsequent interlocking of adjacent discrete portions, had less jig-saw shapes. Changing the quantity of male portions at each cut may alter the flexibility of the shaft at different points along its length. For example, such variation can be used to make the bottom tip portion more or less flexible then the rest of the flexible portion of the shaft.

Figure 8A:
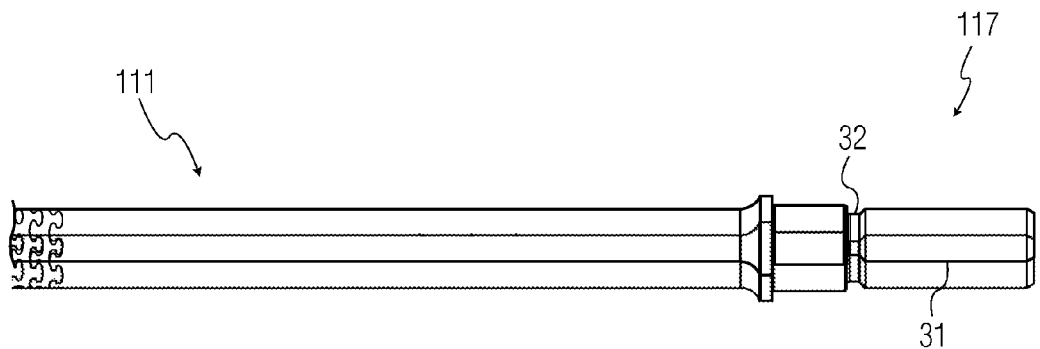
FIGS. 8A-8C illustrate various embodiments of a handle attachment mechanism of an instrument of the present invention.
Figure 8B:
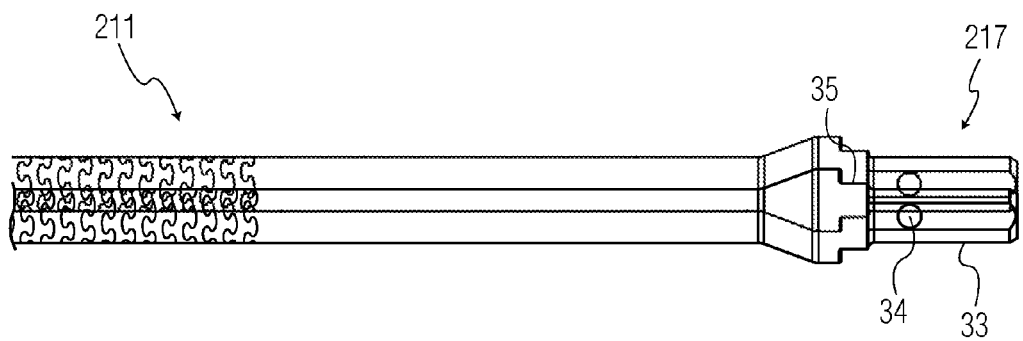
Figure 8C:
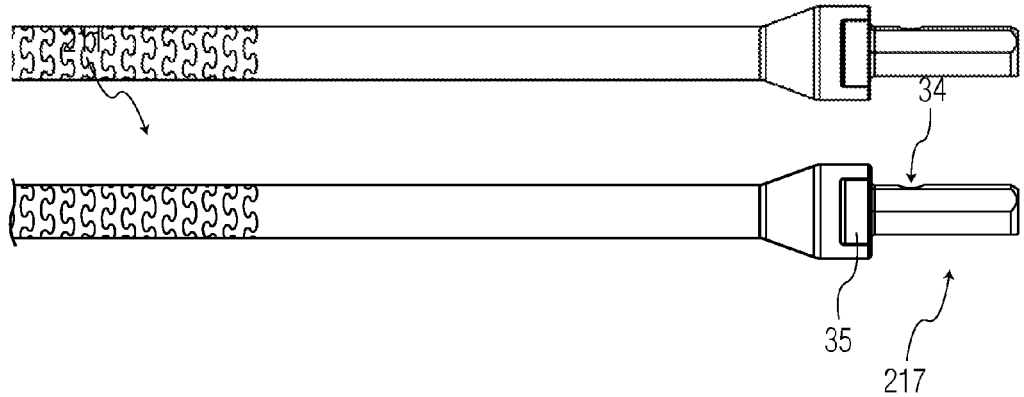

Referring now to FIGS. 8A-C, there are shown two embodiments of shaft 11, generally labeled as 111 and 211. Each embodiment having a different handle attachment mechanism 117 and 217. FIG. 8A illustrates a first embodiment that may be used with a fixed handle. Its attachment mechanism 117 comprises a circular shaft portion 31 that is capable of being inserted into a handle 14. The circular shaft portion 31 includes a groove 32 along the circumference for fixedly securing it to the handle 14.

FIGS. 8B-C illustrate an alternate embodiment of attachment mechanism, labeled 217, which may allow the shaft to be releasably connected to handle 14. This attachment mechanism 217 may include a hexagonal section 33, a notch 35, and a dimple 34. These portions may make up the male portion of the attachment mechanism for inserting into handle 14, which may have corresponding female portions (discussed below as to FIGS. 9A-B) or other structures to releasably secure the handle to the attachment mechanism. Other such handle attachment mechanisms may also be used such that the handle is either fixedly secured to the shaft, and thus they cannot be separated under normal circumstances, or releasably secured, and thus they can be separated by the operator. Such releasable securement may be beneficial where, for example, a single handle is to be used for multiple instruments or where the shaft is disposable and the handle is reusable, or other like considerations.

Figure 9A:
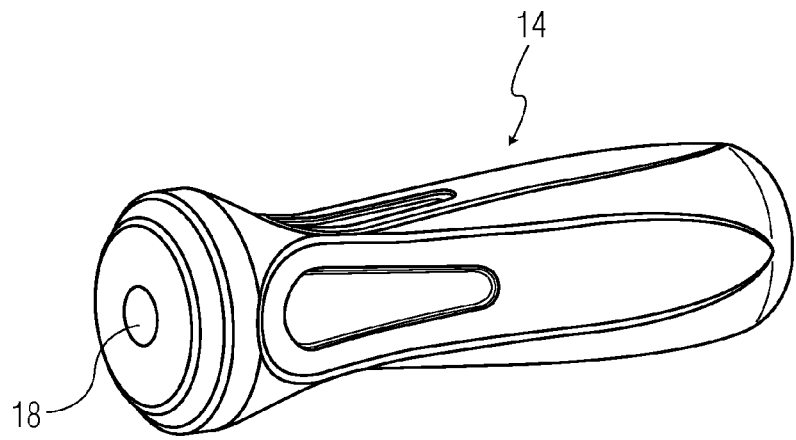
FIGS. 9A and 9B illustrate various embodiments of a handle of an instrument of the present invention.
Figure 9B:
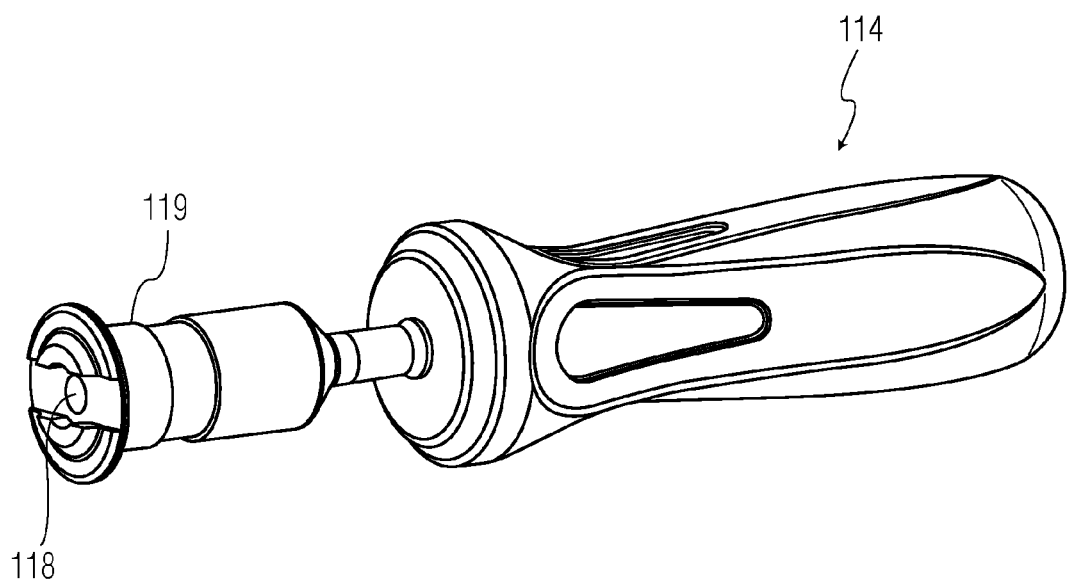

Referring to FIG. 9A-B, there are shown two embodiments of handle 14. FIG. 9A illustrates a fixed handle 14 that extends substantially parallel with the shaft 11. The fixed handle 14 has a shaft attachment mechanism 18 at its distal most point that connects with handle attachment mechanism 17, 117, 217. FIG. 9B illustrates a second embodiment of a handle generally referred to as ratchet handle 114. Ratchet handle 114 is similar to the fixed handle 14 but also includes a ratchet mechanism 119. The ratchet mechanism 119 allows the operator to apply continuous rotational force without re-gripping the handle or disconnecting the driver tip from the anchor.

In an alternate embodiment, ratchet handle 114 may instead have a handle that extends perpendicular (not shown), rather than parallel, with the driver shaft 211. In this alternative embodiment, the cannulation may not extend through the entire driver, i.e., it may not extend through the length of the handle. For example, if the shaft attaches to the head of the ratchet there may only be a need to have the head of the ratchet cannulated, or specifically, may merely have an annular opening through which the proximal end of the shaft 17, 117, 217 may be positioned. This may allow the cannulation of the shaft 11, 111, 211 to be accessible to the operator at the proximal end of the shaft, so there would be no need to have a cannulation along the length of the perpendicular ratchet handle.

In another embodiment of the present invention, as illustrated in FIGS. 10-15, generally, the present invention includes a slide instrument 40 having a slide 50, a handle 44 and a shaft 41 positioned therebetween. The shaft and handle are secured to one another through an engagement structure 47 such as a screw or the like. As will be explained in greater detail below, the slide instrument 40 may be used in conjunction with the driver 10 to protect at least a portion of a graft from a guide wire 70 and/or the interference screw 90 as the screw proceeds along the guide wire and into a bone bore hole alongside the graft.

The slide 50 includes a first channel 51 and a second channel 54 within which the interference screw 90 and the graft, respectively, may reside. The first channel 51 may be sufficiently sized to accommodate various sized interference screws and is defined between first and second channel edges 52, 53. The channel edges 52, 53 may have a similar shape, such that the channel 51 is substantially symmetrical, or the edges may have differing shapes from one another. In any event, the edges, and thus the channel, may have any shape desired. In one example, as illustrated, the first and second channel edges may have differing shapes from one another such that, as illustrated, one of the edges 53 is larger, and thus, extending further away from the trough of the channel, than the other edge 52.

Similarly, the second channel 54 also has third and fourth channel edges 55, 56, and, similarly, they may have any shape desired. As illustrated, for example, the third and fourth edges 55, 56 have differing shapes from one another such that one of the edges 56 is larger than the other edge 55.

The first and second channels 51,54 may have any shape as desired, though, as illustrated, generally curved channels are preferred as they minimize sharp edges or corners which may damage surrounding tissue, or the graft itself, as opposed to a square channel, or the like, which may have sharp edges or corners. Further, the curved first and second channels 51, 54, as illustrated, may be positioned as opposing concave surfaces. Positioning these surfaces to face in opposite directions provides for the slide to maintain separation between the graft and the guide wire, shaft, and/or anchor such that it minimizes contact between the graft and the guide wire, shaft, and/or anchor, discussed further below. Of course, other such shapes may be incorporated into the channels of the slide instrument if so desired. As illustrated, the slide 50 may be designed with larger second and fourth edges 52, 56 to give the first and second channels, and thus the slide as a whole, a lower profile as the slide 50 having such a design can reduce the overall height between the two channels by effectively adjusting the lateral spacing of the two channels and thus decreasing the amount of material required between the two channels. This lateral spacing may result in the first channel being offset from the second channel, as illustrated. Such a lower profile is preferred to minimize its size for insertion through a portal through the skin and into the joint, minimize the amount of volume taken up within the bone tunnel, and the like.

The slide 50 also may include a curve along its length which may coincide with the curve of either or both of the guide wire and/or driver 10. Further, the curve may allow the operator to more easily approach the entrance to the bone tunnel. For example, if approaching the bone tunnel from an anterior direction, the curve of the slide 50 assists the operator in positioning the slide adjacent to or within (at least partially) the bone tunnel because the distal end 57 of the slide is at an approach angle that is closer to parallel with an axis of the bone tunnel than the rest of the slide instrument 40.

Other than serving to separate the guide wire 70 and anchor 90 from the graft 80, the slide may also serve to help ensure that the graft does not tangle around the anchor, guide wire, and/or driver, help ensure that if a threaded anchor is used that the anchor does not "walk" within the bore hole as the anchor is rotated, help ensure that the anchor remains generally parallel to the bore hole, or other such benefits, discussed further below. With these various benefits in mind, the slide 50 may be sized to maintain a low profile while still having sufficient size to protect and manipulate the graft as well as have sufficient strength to assist in maintaining the anchor in a particular position during insertion. Thus, it is preferred that the slide 50, for use in an ACL repair in the femur for example, have a length of up to about 200 mm or less, preferably about 25 mm, a height of about 3 mm to about 10 mm, preferably about 6 mm, and a width of about 5 mm to about 25 mm, preferably about 10 mm, though other dimensions may be desirable in light of certain anatomy or desires of the operator or the size of the bore hole in the bone.

Figure 10:
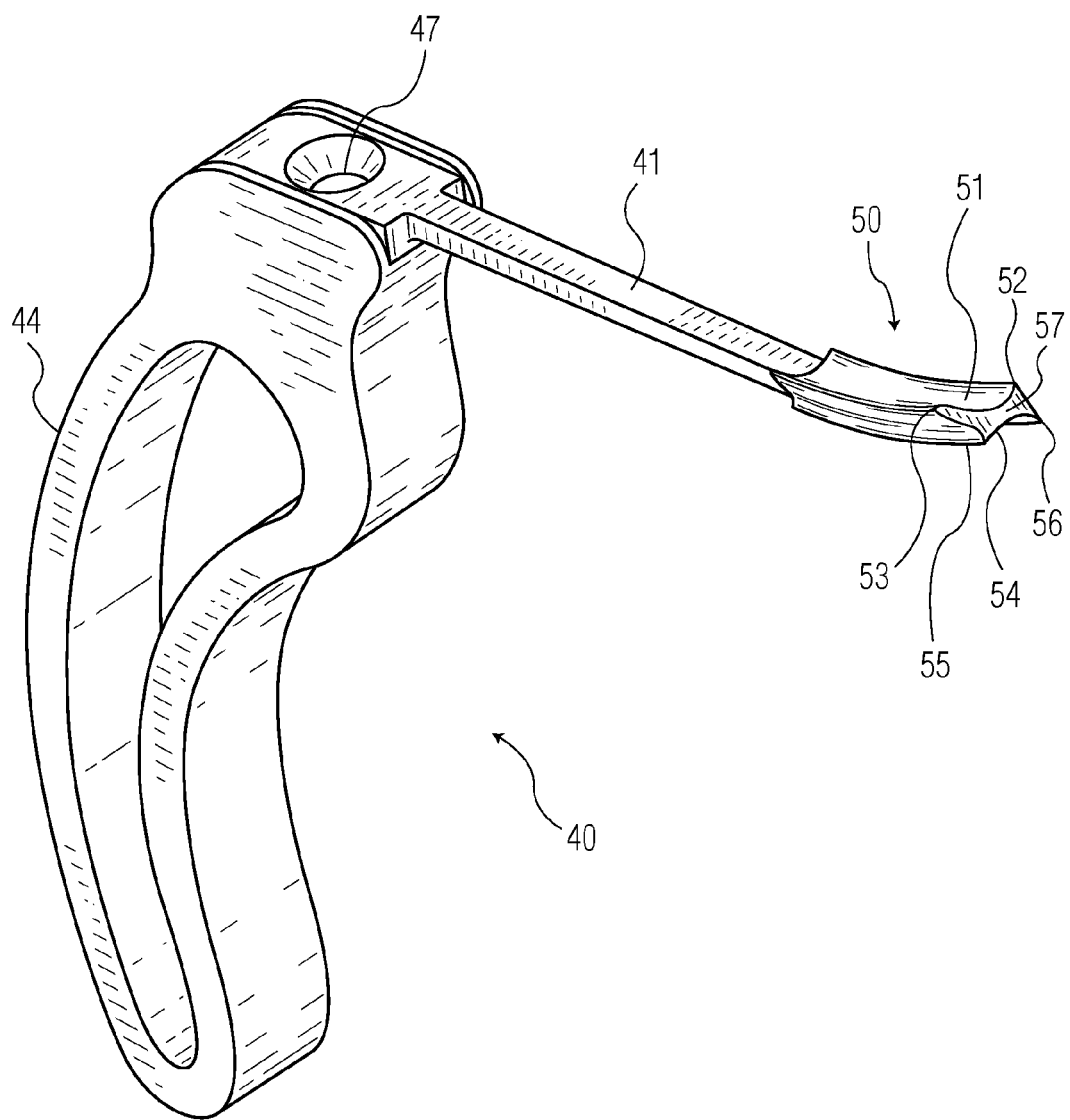
FIG. 10 illustrates another embodiment of an instrument of the present invention.
Figure 11:
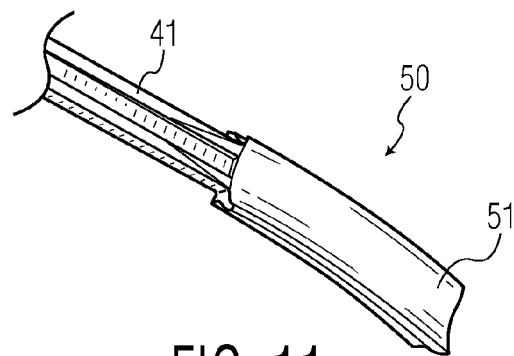
FIGS. 11-15 illustrates various views of a slide of the instrument of FIG. 10.
Figure 12:
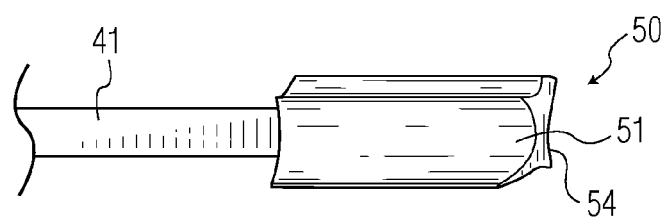
Figure 13:
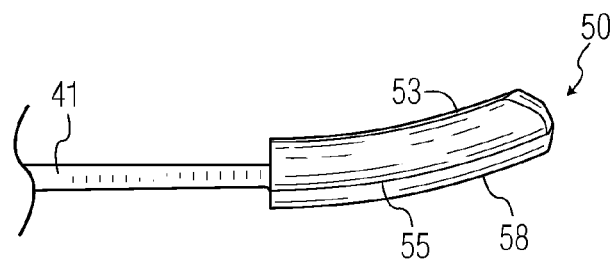
Figure 14:
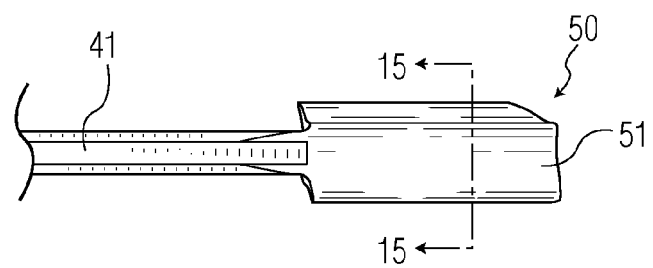
Figure 15:
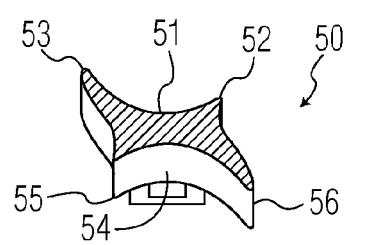
Figure 16:
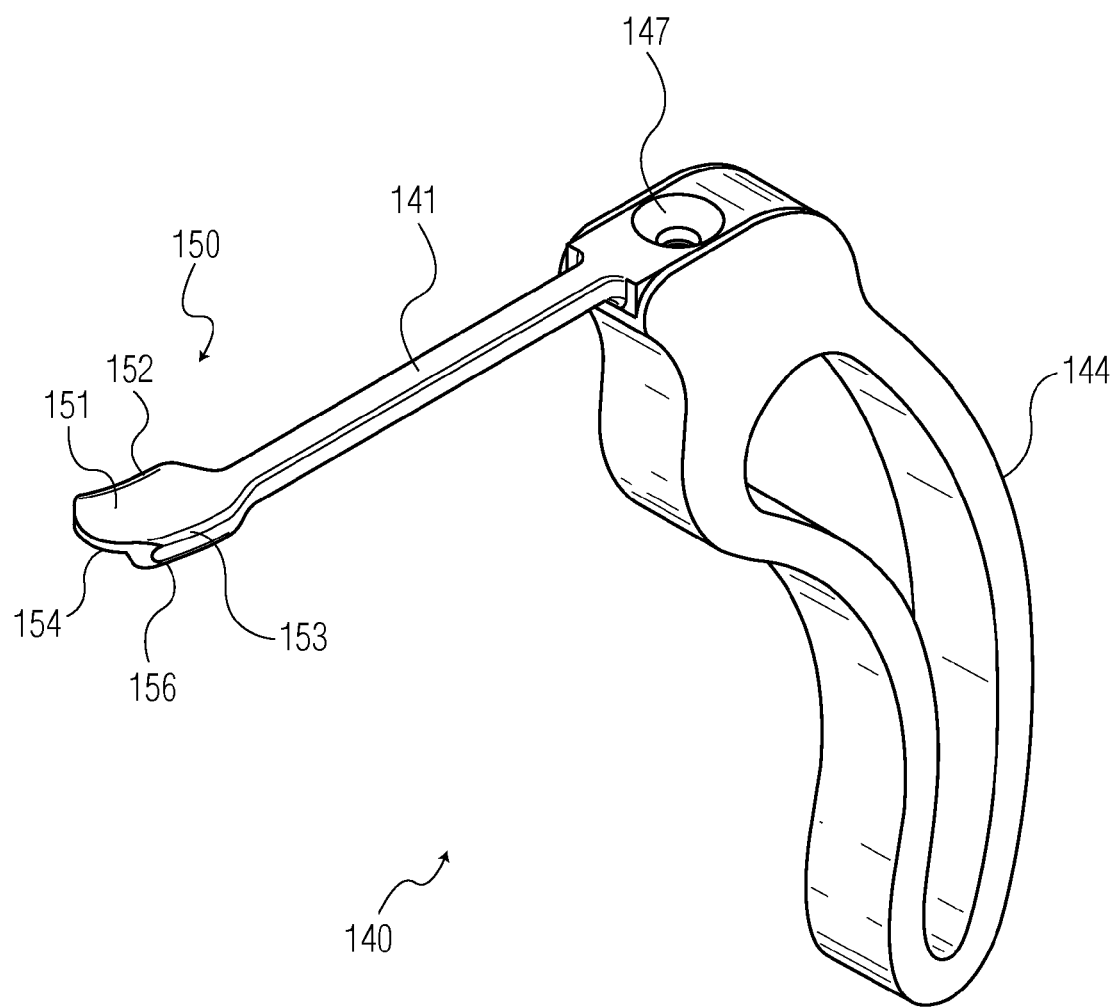
FIG. 16 illustrates a further embodiment of an instrument of the present invention
Figure 17:
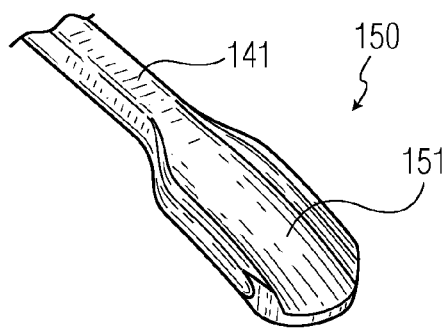
FIGS. 17-21 illustrates various views of a slide of the instrument of FIG. 16
Figure 18:
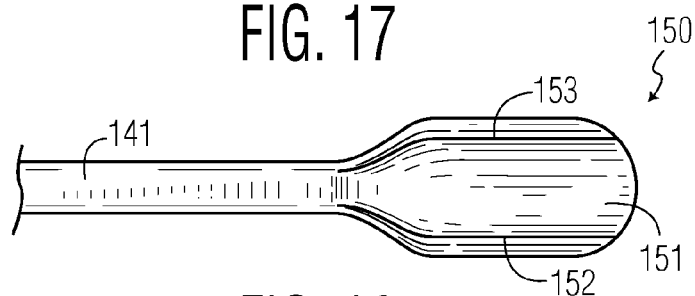
Figure 19:
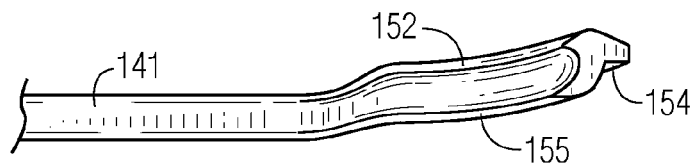
Figure 20:
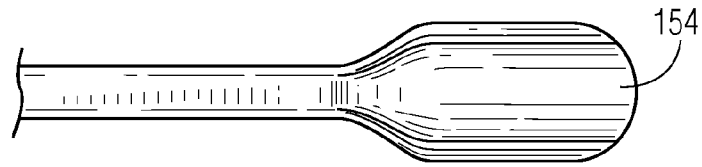
Figure 21:
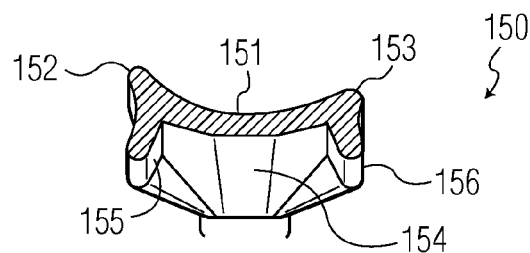

In another embodiment of the slide instrument 140, illustrated in FIGS. 16-22, the slide 150 again includes first and second channels 151, 154, though in this embodiment the first, second, third and fourth channel edges 152, 153, 155, 156 are of a slightly different shape than those of slide 50. For example, as best seen in the cross-sectional views of FIGS. 21 and 22 (both of which are cross-sectional views from a distal position, looking proximally towards handle 144) the first channel 151 includes a defined first channel edge 152 but does not include a well-defined second channel edge 153, and in fact, the second channel edge 153 is all but nonexistent, resulting in the first channel 151, and the slide overall, having a "J" shape, though the portion of the first channel 151 in which the anchor and/or guide wire will be positioned is generally concave in shape. Moreover, the third and fourth channel edges 155, 156 are shorter than the channel edges of the second channel 54 of the slide 50 resulting in a slightly more square-shaped channel 54, though the edges may be softened to minimize sharp edges which could damage the graft material and/or surrounding anatomy. Also, to provide a lower profile shape of slide 150, the second channel 154 includes a convex curve, rather than the concave curve of second channel 54 (FIG. 10). This convex curve may generally follow the concave curve of channel 151 to minimize material between the two channels, resulting in a lower profile design. To maintain the graft within the second channel 154, despite the convex shape, convex channel 154 is bounded by channel edges 155, 156 which may be sized to create an overall concave shape within which the graft may be positioned.

Figure 22:
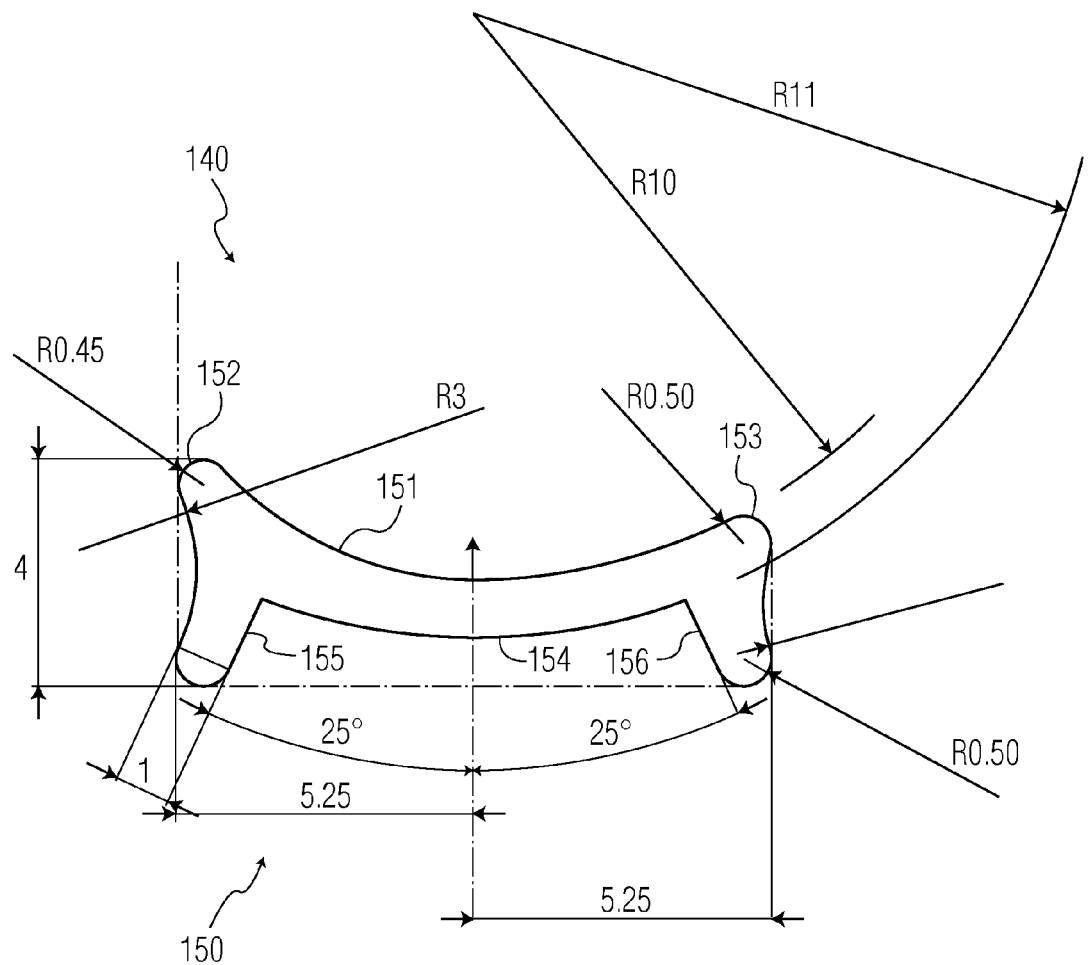
FIG. 22 illustrates a cross-sectional view of the slide of FIGS. 17-21.
Figure 23:
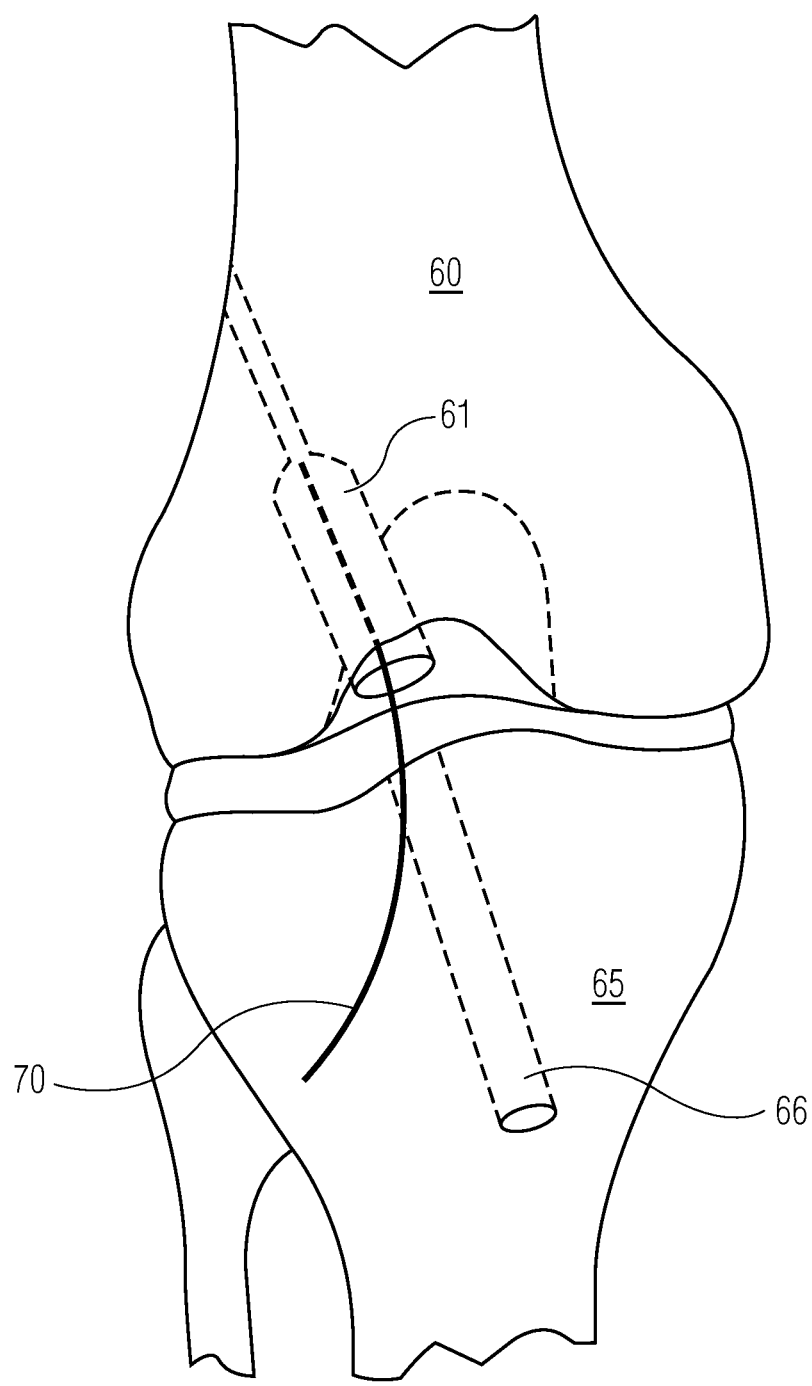
FIGS. 23-26 illustrate one embodiment of a method of the present invention.

Thus, this shape of slide 150 may provide an even smaller cross-sectional shape, and therefore, may result in a slide having a lower profile than slide 50. Further, for example, the lower profile is achieved in the first channel 151 since the anchor rotates clockwise, and thus a pronounced channel edge 152 may only be required on the right-hand side of the slide 150 to prevent the graft material from becoming caught between the "leading" edge of the anchor and the first channel during rotation of the anchor, while such precautions may not be necessary on the left-hand side of the first channel as there is no pinching action between the first channel and the anchor (and thus, channel edge 153 is not as pronounced, allowing for a lower profile slide 150). For example, the height of this slide 150 may be about 4 mm or less (as in FIG. 22, for example), as opposed to slide 50 which may have a height of about 6 mm or less. Such a slide having a low profile, while suitable for use in the knee during ACL repair, may also be useful in the repair of soft tissues in other, smaller, joints, such as the elbow, ankle, or the like. FIG. 22 also lists additional exemplary dimensions as to slide 150, though, again, these dimensions may be altered as desired or required.

Other shapes, configurations, cross-sections and profiles of the slide instrument of the present invention are also envisioned so long as the specific slide instrument is capable of maintaining separation between the graft and the guide wire 70, shaft 11, and/or anchor 90.

The present invention also includes various embodiments of systems and kits for use in soft tissue repair.

In one embodiment, the present invention includes a system for the repair of soft tissue including driver 10, slide instrument 40 and a guide wire 70. The system may also include an anchor 90. Further, the system may optionally include a drill, a pin and/or graft inserter, a notch instrument (all not shown), a tapping instrument (not shown), and other instruments suitable for such repairs. The driver, drill, notch instrument and tapping instrument may each optionally have a shaft including a flexible portion thereon.

The notch instrument may be used to form a notch or "key hole" along a portion of the bore hole. For example, the notch may be along the length of a wall of the bore hole, such that the notch extends substantially parallel along the length of the bore hole. The notch may prevent "walking" of the anchor during insertion. Walking may occur when an interference screw is rotated, and, rather than the threads engaging the wall of the bore hole and gripping and/or digging into the bone (and graft), the threads instead rotate around the circumference of the wall of the bore hole. Such walking may cause entanglement between the driver and the graft. The notch provides a depression within which the interference screw sits and may prevent such walking from occurring by providing a track within which the interference screw can travel, thereby promoting the threads to engage the bone of the bone wall.

The tapping instrument may look similar to the driver 10 with an anchor 90 engaged at its distal end (as in FIG. 5). The tapping instrument may include a distal threaded end, which may be the same size as the anchor to be implanted, though such a size is not necessary, to create a threaded pathway into the bore hole. Then, once the pathway is formed, the tapping instrument is removed and the driver 10 and anchor are inserted such that the anchor may travel along the threaded pathway. Similar to the notching instrument, the tapping instrument may improve the likelihood of a clean and accurate implantation of the anchor by minimizing the chances of the anchor walking within the bore hole. Specifically, the tapping instrument is used when a non-metal anchor is used, such as the Biosteon® Interference Screw discussed above, which may not have a sufficient material strength to form the threads into the bone wall, or the bone portion of a bone-tendon-bone graft, on its own. Moreover, optionally, the tapping instrument may be used even when a titanium implant is used, for example when used to secure a bone-tendon-bone graft. The use of a tapping instrument in this instance may help ensure a clean repair by minimizing the force on the implant required to drive between the bone wall of the bore hole and the bone portion of the graft, thereby lessening the chance of the graft altering its position during insertion of the implant.

In another embodiment, the present invention may include a kit for the repair of soft tissue, the kit including a driver 10, and a plurality of anchors. The plurality of anchors may have various thread size, thread pitch, overall diameter, overall lengths, materials of construction, or other such dimensions, to provide the operator with a variety of anchors such that the operator can select the best option for a particular surgery and/or anatomy. The kit may also include at least one slide instrument. Further, the kit may include at least one guide wire. Additionally, multiple handles 14 may be included, such as one of each of handle 14, ratchet handle 114 and perpendicular ratchet handle (not shown).

In yet another embodiment, the present invention may include a kit for the repair of soft tissue, the kit including a plurality of drivers 10 each having an anchor 90 positioned on a distal tip portion 15 of each driver. Each anchor may have various thread size, thread pitch, overall diameter, overall lengths, materials of construction, or other such dimensions, to provide the operator with a variety of anchors such that the operator can select the best option for a particular surgery and/or anatomy. For example, there may be multiple sizes of polymer-based anchors, of various diameter and/or length, and multiple sizes of titanium, or other metal, anchors of various diameter and/or length. The kit may also include at least one slide instrument. Further, the kit may include at least one guide wire. Additionally, multiple handles 14 may be included, such as one of each of handle 14, ratchet handle 114 and perpendicular ratchet handle (not shown).

The present invention may further include use of the above instruments for performing soft tissue repair including positioning and securing a graft in a bore hole in a bone.

The present invention also includes various methods for positioning and securing a graft in a bore hole formed in a bone. While the exemplary embodiment, illustrated and described herein, is for the positioning and securing of a graft, specifically an anterior cruciate ligament (ACL) graft, in a bone tunnel in a femur, the disclosed instrumentation, devices and methods may be used for the positioning and securing of any graft in any bone. These methods for use in securing an ACL graft may similarly be used, for example, in a method of positioning and securing a posterior cruciate ligament (PCL) graft as well. Further, the bore hole may be a closed end bore hole or a bone tunnel (as illustrated) which passes completely through the bone. Further, as is known in the art, the bone tunnel need can have a constant diameter along its length, though instead, as illustrated in FIGS. 23-26, the tunnel have a first portion of a diameter suitable to contain a graft therein (e.g., about 10 mm), and a second portion of a diameter suitable to contain only a guide wire and/or a length of suture, or the like (e.g., about 2 mm to about 3 mm). The illustrations and discussions herein, therefore, are merely exemplary.

In one embodiment, as illustrated in FIGS. 23-26, the present invention includes a method of positioning and securing a graft 80 within a bore hole 61. Specifically, as illustrated, this method will be described as positioning and securing an anterior cruciate ligament graft 80 within a prepared bone tunnel 61 in a femur 60. It should be noted that, while illustrated the anchor 90 is positioned to the left and the graft 80 and bone block 81 are positioned on the right, the relative positioning of these two elements may be opposite, or otherwise in any orientation as desired within the bone tunnel 61. The bone tunnel 61 may be prepared through any known method, such as those disclosed in co-pending U.S. application Ser. Nos. 12/859,580 and 13/085,882, discussed above. Generally speaking, a pin (not shown) is drilled through the femur, and a flexible drill (not shown) is directed along the pin and through the femur to create the bone tunnel. As illustrated, the flexible drill may only extend partially through the femur along the length of the pin to form a bone tunnel having two sections of different diameter. Once the bone tunnel 61 in the femur 60 is prepared, the pin may be removed and a guide wire 70 may be positioned through an anterior portal 68 through the patient's skin and into at least a portion of the bone tunnel 61 (as shown), or even completely through the entire length of the bone tunnel 61. Alternatively, if the bone tunnel was formed by passing the drill up through a bone tunnel 66 in the tibia 65, then the guide wire may likewise be positioned through the bone tunnel 66 and into bone tunnel 61. The guide wire 70 may be passed through the bone tunnel 61 and exit through the lateral side of the femur 60, or alternatively, as illustrated, may only be positioned in the bone tunnel 61 a sufficient distance to direct the anchor to its secured position within the bone tunnel. The guide wire 70 may include laser marks (not shown) to allow the operator to know how far into the bone tunnel the guide wire is positioned. Of course, if desired, the pin and the guide wire may be the same structure, such that a single pin/guide wire is positioned in the bone tunnel throughout the drilling, positioning and securing steps of this described embodiment.

Figure 24:
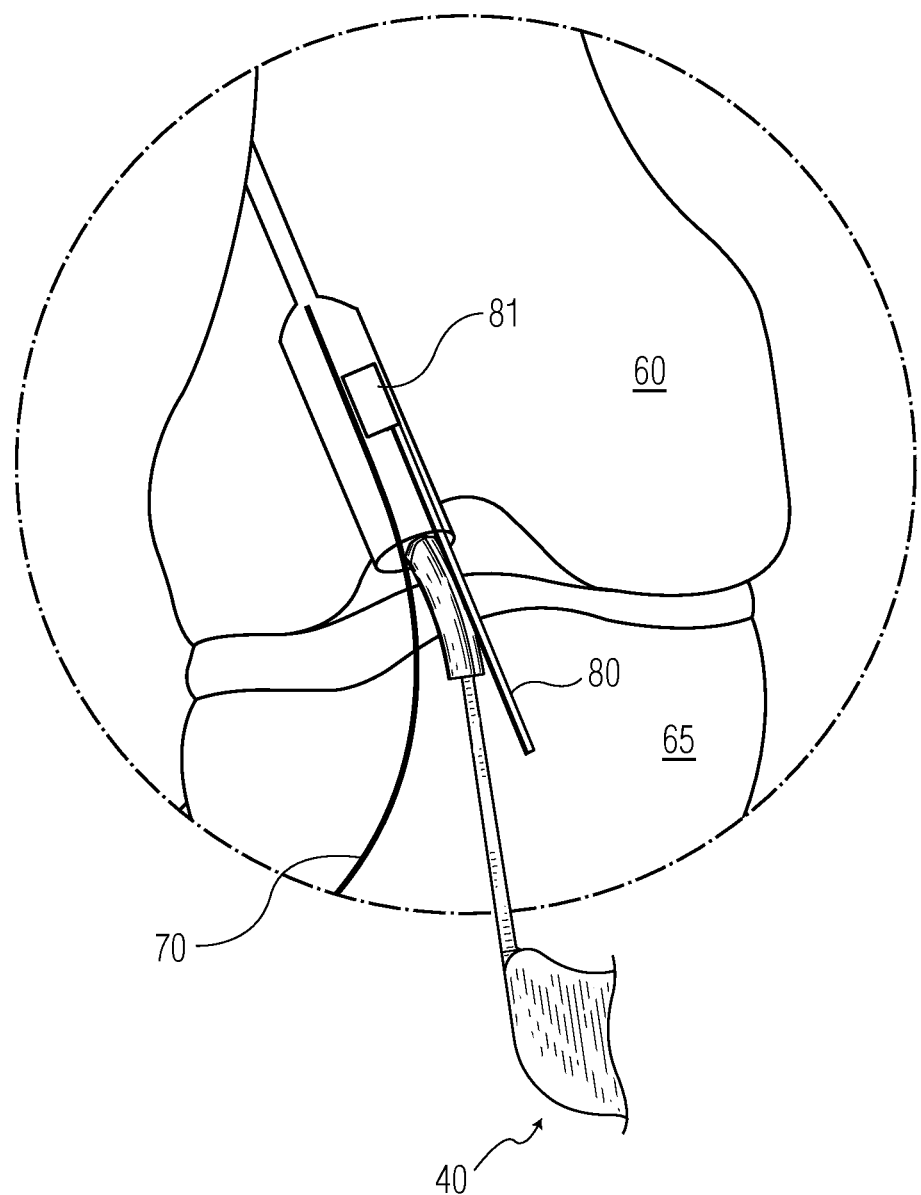

As illustrated in FIG. 24, the ligament graft 80 may also be positioned at least partially in the bone tunnel 61. In this illustration, a bone-tendon-bone graft is used, which includes a bone block 81 on either end of the graft, as is known in the art. An all-soft tissue graft may alternatively be used. It should be noted that the graft 80 may alternatively be positioned in the bone tunnel prior to positioning of the guide wire 70 in the bone tunnel, such that these steps may be interchangeable with one another based on preference. The graft may be positioned into the bone tunnel using a length of suture secured to the graft and led up through the bone tunnel and out the lateral side. The suture may then be pulled to pull the graft into the bone tunnel. If a bone-tendon-bone graft is used, the suture may be threaded through the bone, or otherwise secured to the bone to be secured within the femur tunnel. If an all-soft tissue graft is used, the graft may be folded in half and a suture passed through the fold, which may then be pulled into the tunnel such that the two ends of the graft extend out of the tunnel, to later be secured in the tibia.

In yet another alternative, the pin, on which the drill travels to form the bone tunnel, may include an eyelet or like structure on a proximal end. This eyelet may be used to pass the suture, and thus the graft, into the bone tunnel once the drill is removed. This step may, for the sake of convenience, be performed prior to directing the guide wire 70 into the bone tunnel, though again, these steps are interchangeable as desired.

Once both the guide wire 70 and graft 80 are positioned in the bone tunnel 61, the slide 50 of a slide instrument 40 may be positioned at the entrance of the bone tunnel 61, or at least partially within the bone tunnel, such that it is positioned between the graft 80 and the guide wire 70, as illustrated in FIG. 24. As discussed above, preferably, the guide wire 70 may be positioned at least partially within the first channel 51, or on the side of the slide 50 adjacent the first channel, and the graft may be positioned at least partially within the second channel 54, or on the side of the slide 50 adjacent the second channel (of course, slide 150 may alternatively be used). As such, the slide 50 effectively divides the bore hole in the bone, along the length of the slide 50, into a first side and a second side, such that the guide wire (on the first side, for example) does not contact the graft (on the second side, for example) along the length of the slide. The step of positioning the slide may alternatively be performed prior to both the graft and guide wire being positioned in the bone tunnel, or in between these two steps, which also may be interchanged with one another, as desired by the operator.

Figure 25:
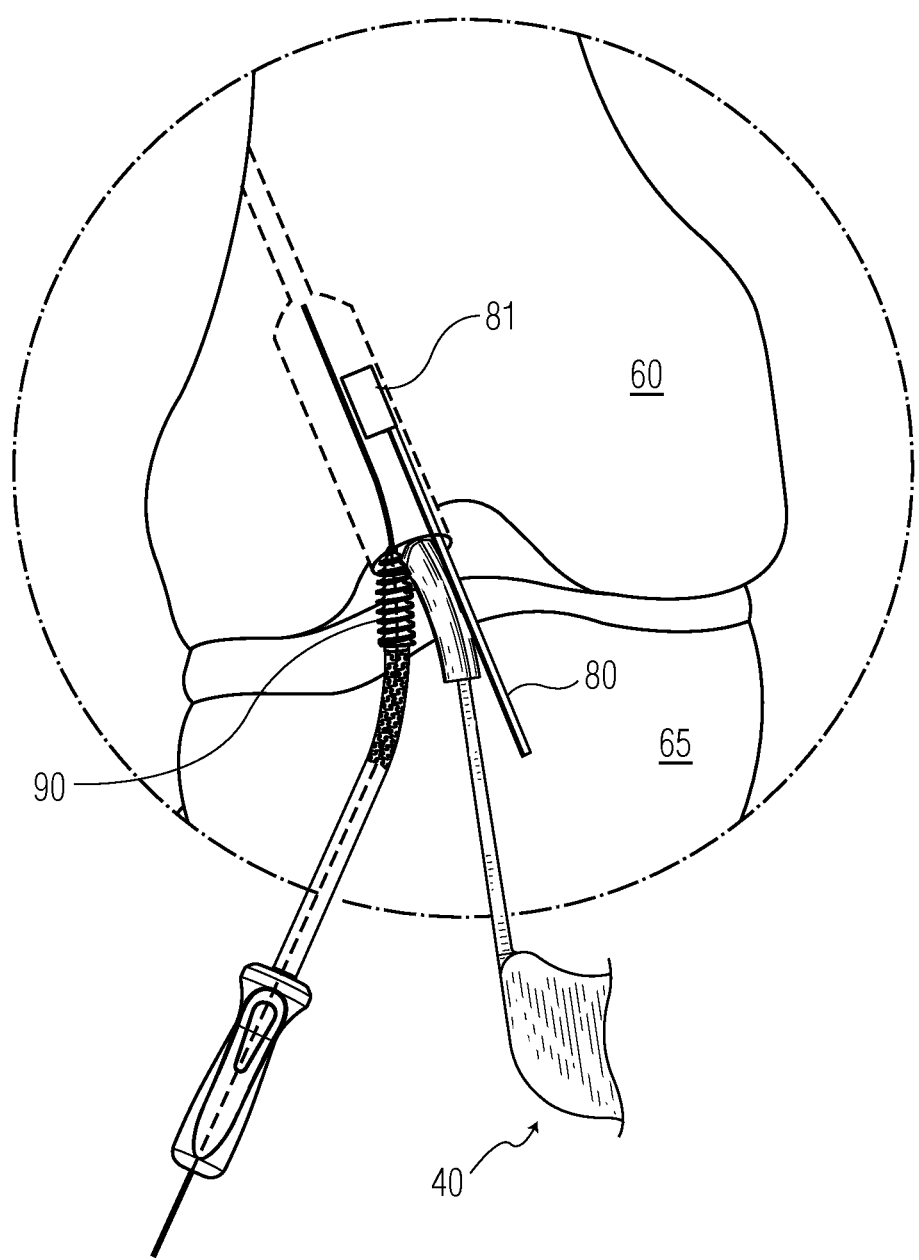

The driver 10, and attached anchor 90, may then be positioned over the guide wire 70, by passing the end of the guide wire through the cannulation of the anchor and driver, such that the anchor and driver may slide along the guide wire and direct the anchor towards the bone tunnel 61. As illustrated in FIG. 25, as the anchor 90 approaches the bone tunnel 61 along the guide wire 70, it may be positioned within the first channel 51 of the slide 50, and thus, on the first side of the bone tunnel. At this point, the anchor 90 and graft 80 are separated from one another by slide 50 such that they do not contact one another. Such separation may prevent the anchor from damaging the graft 80 tissue, may allow for continued manipulation of either or both of the graft and anchor by the slide 50 and/or driver 10, and the like.

Figure 26:
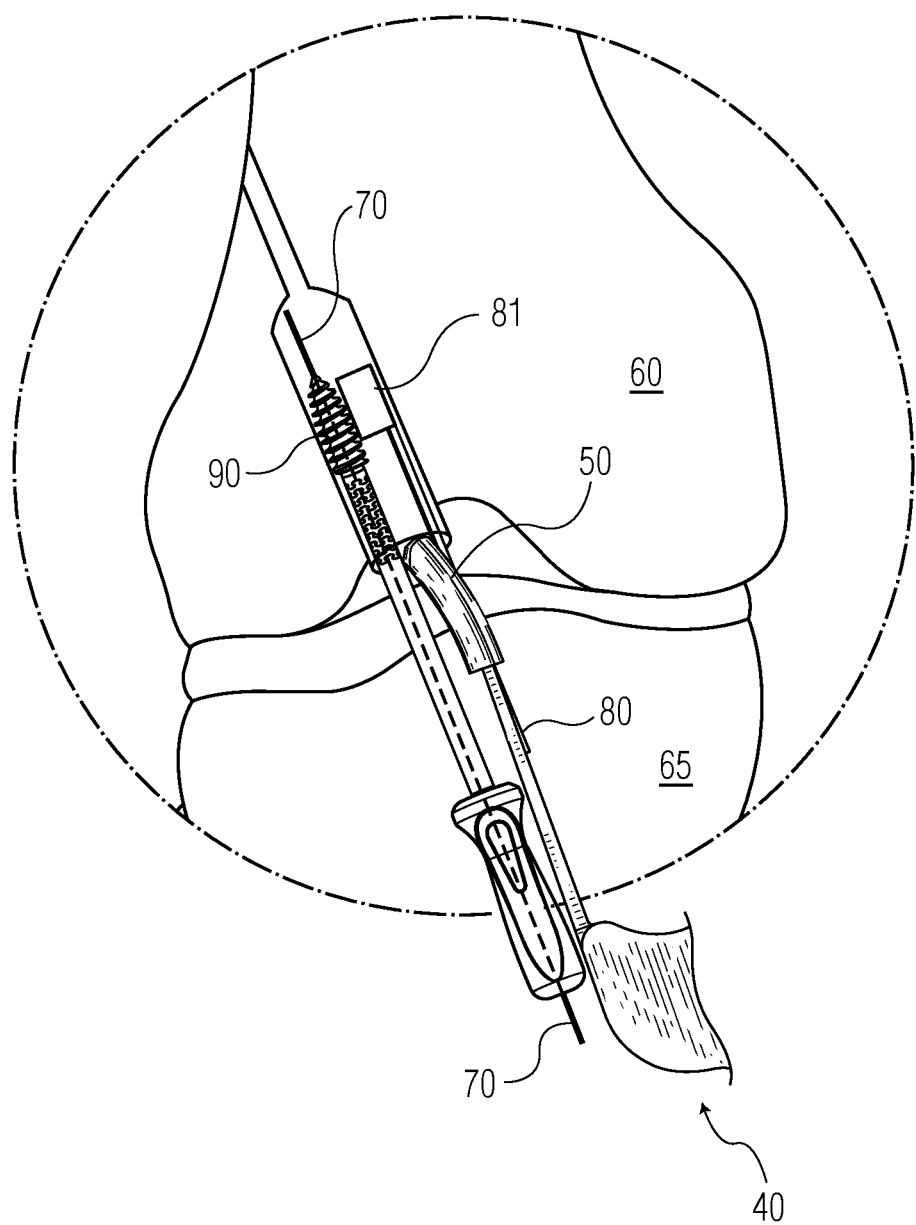

The slide 50 may remain in position as the anchor 90 is continuously directed further into the bone tunnel until the anchor 90 is adjacent the portion of the graft intended to be contacted, and secured, by the anchor, as is illustrated in FIG. 26. Upon attaining this position, the anchor 90 is secured in place by the driver 10. For example, using the illustrated example of the anchor as an interference screw 90, the driver may be rotated to impart rotation on the interference screw 90 which may cause the threading on the outer surface of the interference screw to engage both the bone tissue of the bone tunnel 61 side wall and the tissue of the graft 80, such as the bone block 81 of the bone-tendon-bone graft as illustrated. Alternatively, of course, if an all-soft tissue graft 80 is used the interference screw threads would instead engage a portion of the soft tissue of the graft to cause an interference fit between the screw, graft and sidewall of the bone tunnel.

Once the graft 80 is secured within bone tunnel 61, the instrumentation, including the driver and slide, may be removed. Next, the opposing end of the graft may be secured within the bone tunnel 66 of tibia 65 by the same method or, alternatively, by other techniques known in the art. The guide wire 70 may be removed from bone tunnel 61 at any time once the length of the anchor 90 is positioned about halfway into the bone tunnel entrance.

In one variation to the above embodiment, prior to placing anchor 90 into the bone tunnel 61, and optionally prior to positioning either or both of the graft 80 and guide wire 70 in the bone tunnel 61, a notch (not shown) may be formed in the side wall of the bone tunnel 61 by a notching instrument (not shown). In one example, the notch may extend along at least a portion of the length of the bone tunnel, and may be generally linear, and generally parallel to the axis of the bone tunnel. This notch may assist the anchor, particularly one which must be rotated such as a threaded interference screw, in maintaining a desired position within the bone tunnel and not walking.

In another variation the tapping instrument (not shown) may be used to create a tap on the wall of the bone tunnel and also on the bone 81 of a bone-tendon-bone graft (if used). This step of tapping may be used when a polymer anchor 90 is going to be used and/or when a bone-tendon-bone graft is going to be used.

In yet a further variation, the operator may desire to include additional fixation of the graft, using an additional anchor such as the VersiTomic G-Loc implant (Howmedica Osteonics Corp., Mahwah, N.J.), also variously disclosed in U.S. Pending application Ser. No. 12/682,324, filed Oct. 9, 2008, Ser. No. 13/182,851, filed Jul. 14, 2011, and Ser. No. 13/070,692, filed Mar. 24, 2011, all of which are owned by the same assignee as this application, and all of which are incorporated by reference herein as if fully set forth herein. If such an additional anchor is used, the graft may be positioned within the bone tunnel 61 as this additional implant is positioned through the bone tunnel and to the lateral side of the femur upon exiting the bone tunnel. Thus, if such an implant is used, the graft would be secured to the implant as is typically done using such implants, and the implant is positioned at the entrance to the bone tunnel. As the implant is positioned into the bone tunnel, the implant drags the graft with it, thereby moving the graft into position, as discussed above. Such a variation may replace the need to use the other steps, discussed above, to position the graft such as using an eyelet on the pin or positioning a suture through the bone tunnel to pull the graft into place.

In a further embodiment, the present invention may also include a method of providing instructions or information to practice any of the various methods of performing soft tissue repair as described herein. For example, the method may include supplying a surgical protocol, or like document, to provide step-by-step instructions for performing any of the method embodiments of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for positioning and securing a graft in a prepared bone hole, the method comprising:
    advancing at least a first portion of the graft into the bone hole;
    passing a flexible guide wire into the bone hole;
    positioning a slide instrument between the graft and flexible guide wire such that the slide instrument separates the bone hole into a first side and a second side, such that the graft is positioned within the first side of the bone hole and the flexible guide wire is positioned within the second side of the bone hole;
    positioning a cannulated driver, having a flexible portion, and a cannulated anchor, engaged with a distal end of the cannulated driver, over the guide wire such that the guide wire is positioned within the cannulated anchor and at least a portion of the cannulated driver;
    directing the cannulated anchor along the guide wire and into the second side of the bone hole; and
    fixedly securing the graft in the bone hole by positioning the anchor between a portion of a bone wall of the bone hole and at least part of the first portion of the graft, wherein the part of the first portion of the graft is compressed between another portion of the bone wall of the bone hole and the anchor.

2. The method of claim 1, wherein the slide minimizes contact between the anchor and an at least second portion of the graft.

3. The method of claim 1, wherein the bone hole is a bone tunnel formed in a distal portion of a femur.

4. The method of claim 3, wherein the graft is a replacement anterior cruciate ligament (ACL) graft.

5. The method of claim 1, wherein the anchor is a threaded interference screw, wherein the directing and fixedly securing steps include rotating the threaded interference screw such that the threads of the threaded interference screw engage both the part of the first portion of the graft and the portion of the bone wall of the bone hole.

6. The method of claim 1, wherein a notch is formed along at least part of the portion of the bone wall of the bone hole either prior to the step of advancing the graft or after the step of positioning the slide, wherein the notch maintains the position of the anchor against the portion of the bone wall of the bone hole.

7. A method of positioning and securing a graft to bone comprising:
    positioning the graft into a bore hole in the bone;
    positioning a guide wire into the bore hole in the bone;
    positioning a slide instrument between the guide wire and the graft;
    positioning a driver, and an anchor secured thereto, over the guide wire;
    directing the anchor along the guide wire and towards and into the bore hole; and
    imparting a rotational force to the anchor to secure the anchor between a sidewall of the bore hole and a portion of the graft.

8. The method of claim 7, wherein the slide includes a first channel and a second channel, wherein the guide wire is positioned within the first channel and the graft is positioned within the second channel such that the guide wire and graft remain separated from one another.

9. The method of claim 8, wherein, as the anchor is directed towards and into the bore hole, the anchor and graft remain separated from one another.

10. The method of claim 9, wherein as the anchor is directed further into the bore hole, the anchor is directed past the slide to contact the portion of the graft.

11. The method of claim 8, wherein the first channel includes a concave surface and the second channel includes a concave surface positioned in a direction opposite the first channel.

12. The method of claim 8, wherein the first channel includes a concave surface and the second channel includes a convex surface, wherein the convex surface is bounded between first and second channel edges.

13. The method of claim 7, wherein prior to directing the anchor towards and into the bore hole, forming a notch along at least a portion of the length of the bore hole, such that the anchor is directed along the notch within the bore hole.

14. The method of claim 7, wherein the guide wire includes a curve along at least a portion of its length between a point where the guide wire enters the bore hole and an end of the guide wire, positioned outside the bone.

15. The method of claim 14, wherein the driver includes a portion of a shaft that is flexible such that the driver can be directed over the curve in the guide wire.

16. The method of claim 7, wherein the anchor is an interference screw including a threading along at least a portion of its outer surface, wherein upon imparting the rotational force, the threading engages the sidewall of the bore hole and the portion of the graft.

17. The method of claim 16, wherein the graft comprises a bone-tendon-bone graft, and the portion of the graft engaged by the threading of the interference screw is bone.

18. The method of claim 7, wherein the bore hole is a bone tunnel and the bone is a femur, wherein the graft is a replacement anterior cruciate ligament graft.

19. A method of positioning and securing a graft to bone comprising:
- positioning a flexible guide wire into a bore hole in the bone, the flexible guide wire having a length;
- positioning the graft into the bore hole in the bone;
- positioning a driver, and an anchor secured thereto, over the flexible guide wire, the driver including a shaft, at least a portion of which is flexible;
- directing the anchor along the flexible guide wire and into the bore hole; and
- imparting a rotational force to the anchor to secure the anchor between a sidewall of the bore hole and a portion of the graft.

20. The method of claim 19, further including the step of positioning a slide between the flexible guide wire and the graft prior to the step of positioning the driver and anchor over the guide wire.

21. The method of claim 20, wherein the slide includes a first channel and a second channel, wherein the guide wire is positioned within the first channel and the graft is positioned within the second channel such that the guide wire and graft remain separated from one another.

* * * * *